(12) United States Patent
Watanabe et al.

(10) Patent No.: US 7,723,567 B1
(45) Date of Patent: May 25, 2010

(54) RAFFINOSE SYNTHASE GENES AND THEIR USE

(75) Inventors: Eijiro Watanabe, Takarazuka (JP); Kenji Oeda, Kyoto (JP)

(73) Assignee: Sumitomo Chemical Company, Limited, Osaka-fu (JP)

( * ) Notice: Subject to any disclaimer, the term of this patent is extended or adjusted under 35 U.S.C. 154(b) by 0 days.

(21) Appl. No.: 08/992,914

(22) Filed: Dec. 18, 1997

(30) Foreign Application Priority Data

Dec. 18, 1996 (JP) ................................. 8-338673

(51) Int. Cl.
*C12N 15/82* (2006.01)
*C12N 15/29* (2006.01)

(52) U.S. Cl. .................. 800/284; 435/320.1; 536/23.2; 536/23.6

(58) Field of Classification Search ............... 536/23.6, 536/23.1, 295; 800/278, 284, 298; 435/69.1, 435/468, 208, 410, 419
See application file for complete search history.

(56) References Cited

U.S. PATENT DOCUMENTS 5,710,365 A 1/1998 Kerr et al.
6,166,292 A * 12/2000 Osumi et al. ................ 800/284
6,891,084 B1 * 5/2005 Osumi et al. ................ 800/298

FOREIGN PATENT DOCUMENTS

EP 0 293 358 A2 11/1988
WO 9849273 A1 11/1998

OTHER PUBLICATIONS

Napoli et al. The Plant Cell. 1989. vol. 2: 278-289.*
Carvalho et al. The EMBO J. 1992. vol. 11: 2995-2602.*
Ejdeback et al. Protein Expression and Purifification. 1997. vol. 11: 17-25.*
Richmond et al 2000, Plant Physiology 124: 495-498.*
Peterbauer et al 2002, Planta 215: 839-846.*
Duggleby 1997, Gene 190: 245-249.*
Castillo, et al., "Raffinose Synthase and Galactinol Synthase in Developing Seeds and Leaves of Legumes," J. Agric. Food Chem. (1990) vol. 38, p.p. 351-355.
Lehle, et al., "The Function of myo-Inositol in the Biosynthesis of Raffinose," Eur. J. Biochem. .(1973) vol. 38, p.p. 103-110.

* cited by examiner

*Primary Examiner*—David H Kruse
(74) *Attorney, Agent, or Firm*—Birch, Stewart, Kolasch & Birch, LLP

(57) ABSTRACT

Raffinose synthase genes coding for proteins capable of producing raffinose by combining a D-galactosyl group through an α(1→6) bond with a hydroxyl group attached to the carbon atom at position 6 of a D-glucose residue in a sucrose molecule were isolated from various plants. These raffinose synthase genes are useful to change the content of raffinose family oligosaccharides in plants.

6 Claims, 3 Drawing Sheets

RAFFINOSE SYNTHASE GENES AND THEIR USE

FIELD OF INVENTION

The present invention relates to raffinose synthase genes and their use.

PRIORITY

This Application claims priority under 35 U.S.C. §119 to Japanese Application No. 8-338673 filed on Dec. 18, 1996.

BACKGROUND OF THE INVENTION

Raffinose family oligosaccharides are derivatives of sucrose, which are represented by o-α-D-galactopyranosyl-(1→6) n-o-α-D-glucopyranosyl-(1→2)-β-D-fluctofuranoside as the general formula, and they are designated "raffinose" when n=1, "stachyose" when n=2, "verbascose" when n=3, and "ajugose" when n=4.

The greatest contents of such raffinose family oligosaccharides are found in plants, except for sucrose, and it has been known that they are contained not only in higher plants including gymnosperms such as pinaceous plants (e.g., spruce) and angiosperms such as leguminous plants (e.g., soybean, kidney bean), brassicaceous plants (e.g., rape), chenopodiaceous plants (e.g., sugar beet), malvaceous plants (e.g., cotton), and salicaceous plants (e.g., poplar), but also in green algae, *chlorella*. Thus, they occur widely in the plant kingdom similarly to sucrose.

Raffinose family oligosaccharides play a role as reserve sugars in the storage organs or seeds of many plants or as translocating sugars in the phenomenon of sugar transportation between the tissues of some plants.

Furthermore, it has been known that raffinose family oligosaccharides have an effect of giving good conditions of enterobacterial flora, if present at a suitable amount in food. Therefore, raffinose family oligosaccharides have already been used as a functional food material for addition to some kinds of food and utilized in the field of specified healthful food.

Raffinose family oligosaccharides having such a role and utility are produced by the raffinose oligosaccharide synthesis system beginning with sucrose in many plants. This biosynthesis system usually involves a reaction for the sequential addition of galactosyl groups from galactotinol through an α(1→6) bond to a hydroxyl group attached to the carbon atom at position 6 of a D-glucose residue in a sucrose molecule.

In the first step of this biosynthesis system, raffinose synthase is an enzyme concerned in the reaction of raffinose production by combining a D-galactosyl group from galactotinol through an α(1→6) bond with a hydroxyl group attached to the carbon atom at position 6 of a D-glucose residue in a sucrose molecule. It has been suggested that this enzyme constitutes a rate limiting step in the above synthesis system, and it has been revealed that this enzyme is quite important in the control of biosynthesis of raffinose family oligosaccharides.

The control of expression level or activity of raffinose synthase in plants makes it possible to change the contents of raffinose family oligosaccharides in these plants. However, raffinose synthase, although the presence of this enzyme itself was already confirmed in many plants by the measurement of its activity with a biochemical technique, has not yet been successfully isolated and purified as a homogeneous protein. In addition, the amino acid sequence of this enzyme is still unknown, and no report has been made on an attempt at beginning to isolate a gene coding for this enzyme.

SUMMARY OF THE INVENTION

Under these circumstances, the present inventors have intensively studied and finally succeeded in isolating a raffinose synthase and a gene coding for this enzyme from broad bean, thereby completing the present invention.

Thus, the present invention provides the following:

1) A raffinose synthase gene isolated from a plant and having a nucleotide sequence coding for an amino acid sequence of a protein capable of producing raffinose by combining a D-galactosyl group through an α(1→6) bond with a hydroxyl group attached to the carbon atom at position 6 of a D-glucose residue in a sucrose molecule.

2) The raffinose synthase gene according to item 1, wherein the plant is a dicotyledon.

3) The raffinose synthase gene according to item 2, wherein the dicotyledon is a leguminous plant.

4) The raffinose synthase gene according to item 3, wherein the leguminous plant is broad bean.

5) A raffinose synthase gene having a nucleotide sequence coding for protein (a) or (b) as defined below:

(a) protein having the amino acid sequence of SEQ ID NO:2;

(b) protein having an amino acid sequence derived by deletion, replacement, modification or addition of one or several amino acids in the amino acid sequence of SEQ ID NO:2 and capable of producing raffinose by combining a D-galactosyl group through an α(1→6) bond with a hydroxyl group attached to the carbon atom at position 6 of a D-glucose residue in a sucrose molecule.

6) A raffinose synthase gene having the nucleotide sequence of SEQ ID NO:1.

7) The raffinose synthase gene according to item 3, wherein the leguminous plant is soybean.

8) A raffinose synthase gene having a nucleotide sequence coding for protein (a) or (b) as defined below:

(a) protein having the amino acid sequence of SEQ ID NO:4;

(b) protein having an amino acid sequence derived by deletion, replacement, modification or addition of one or several amino acids in the amino acid sequence of SEQ ID NO:4, and capable of producing raffinose by combining a D-galactosyl group through an α(1→6) bond with a hydroxyl group attached to the carbon atom at position 6 of a D-glucose residue in a sucrose molecule.

9) A raffinose synthase gene having the nucleotide sequence of SEQ ID NO:3.

10) The raffinose synthase gene according to item 2, wherein the dicotyledon is a lamiaceous plant.

11) The raffinose synthase gene according to item 10, wherein the lamiaceous plant is Japanese artichoke.

12) A raffinose synthase gene having a nucleotide sequence coding for the amino acid sequence of SEQ ID NO:6.

13) A raffinose synthase gene having the nucleotide sequence of SEQ ID NO:5.

14) The raffinose synthase gene according to item 1, wherein the plant is a monocotyledon.

15) The raffinose synthase gene according to item 14, wherein the monocotyledon is a gramineous plant.

16) The raffinose synthase gene according to item 15, wherein the gramineous plant is corn.

17) A raffinose synthase gene having a nucleotide sequence coding for the amino acid sequence of SEQ ID NO:8.

18) A raffinose synthase gene having the nucleotide sequence of SEQ ID NO:7.

19) A raffinose synthase protein having amino acid sequence (a) or (b) as defined below:
(a) amino acid sequence of SEQ ID NO:2 or SEQ ID NO:4;
(b) amino acid sequence derived by deletion, replacement, modification or addition of one or several amino acids in the amino acid sequence of SEQ ID NO:2 or SEQ ID NO:4;
the protein being capable of producing raffinose by combining a D-galactosyl group through an α(1→6) bond with a hydroxyl group attached to the carbon atom at position 6 of a D-glucose residue in a sucrose molecule.

20) A raffinose synthase protein having the amino acid sequence of SEQ ID NO:2 or SEQ ID NO:4.

21) A gene fragment having a partial nucleotide sequence of the raffinose synthasegene of item 1, 2, 3, 4, 7, 10, 11, 14, 15 or 16.

22) A gene fragment having a partial nucleotide sequence of the raffinose synthase gene of item 5, 6, 8, 9, 12, 13, 17 or 18.

23) The gene fragment according to item 21 or 22, wherein the number of nucleotides is in the range of from 15 to 50.

24) A method for the detection of a raffinose synthase gene or a gene fragment having a partial nucleotide sequence thereof, which comprises hybridizing a probe of the labeled gene fragment of item 21, 22 or 23 to an organism-derived genomic DNA or cDNA fragment; and detecting the DNA fragment bound specifically to the probe.

25) A method for the detection of a raffinose synthase gene or a gene fragment having a partial nucleotide sequence thereof, which comprises hybridizing a probe of the labeled gene fragment of item 21, 22 or 23 to a plant-derived genomic DNA or cDNA fragment; and detecting the DNA fragment bound specifically to the probe.

26) A method for the amplification of a raffinose synthase gene or a gene fragment having a partial nucleotide sequence thereof, which comprises annealing a primer having a nucleotide sequence of the gene fragment of item 21, 22 or 23 to organism-derived genomic DNA or cDNA; and amplifying the resulting DNA fragment by polymerase chain reaction.

27) A method for the amplification of a raffinose synthase gene or a gene fragment having a partial nucleotide sequence thereof, which comprises annealing a primer having a nucleotide sequence of the gene fragment of item 21, 22 or 23 to plant-derived genomic DNA or cDNA; and amplifying the resulting DNA fragment by polymerase chain reaction.

28) A method for obtaining a raffinose synthase gene, comprising the steps of identifying a DNA fragment containing a raffinose synthase gene or a gene fragment having a partial nucleotide sequence thereof by the method of item 24, 25, 26 or 27; and isolating and purifying the DNA fragment identified.

29) A raffinose synthase gene obtained by identifying a DNA fragment containing a raffinose synthase gene or a gene fragment having a partial nucleotide sequence thereof by the method of item 24, 25, 26 or 27; and isolating and purifying the DNA fragment identified.

30) A chimera gene comprising the raffinose synthase gene of item 1, 2, 3, 4, 5, 6, 7, 8, 9, 10, 11, 12, 13, 14, 15, 16, 17, 18 or 29, and a promoter linked thereto.

31) A transformant obtained by introducing the chimera gene of item 30 into a host organism.

32) A plasmid comprising the raffinose synthase gene of item 1, 2, 3, 4, 5, 6, 7, 8, 9, 10, 11, 12, 13, 14, 15, 16, 17, 18, 29 or 30.

33) A host organism transformed with the plasmid of item 32, or a cell thereof.

34) A microorganism transformed with the plasmid of item 32.

35) A plant transformed with the plasmid of item 32, or a cell thereof

36) A method for metabolic modification, which comprises introducing the raffinose synthase gene of item 1, 2, 3, 4, 5, 6, 7, 8, 9, 10, 11, 12, 13, 14, 15, 16, 17, 18, 29 or 30 into a host organism or a cell thereof, so that the content of raffinose family oligosaccharides in the host organism or the cell thereof is changed.

37) A method for the production of a raffinose synthase protein, which comprises isolating and purifying a raffinose synthase protein from a culture obtained by cultivating the microorganism of item 34.

38) An anti-raffinose synthase antibody capable of binding to the raffinose synthase protein of item 19 or 20.

39) A method for the detection of a raffinose synthase protein, which comprises treating a test protein with the anti-raffinose synthase antibody of item 38; and detecting the raffinose synthase protein by antigen-antibody reaction between the antibody and the raffinose synthase protein.

DETAILED DESCRIPTION OF THE INVENTION

Figure 1:
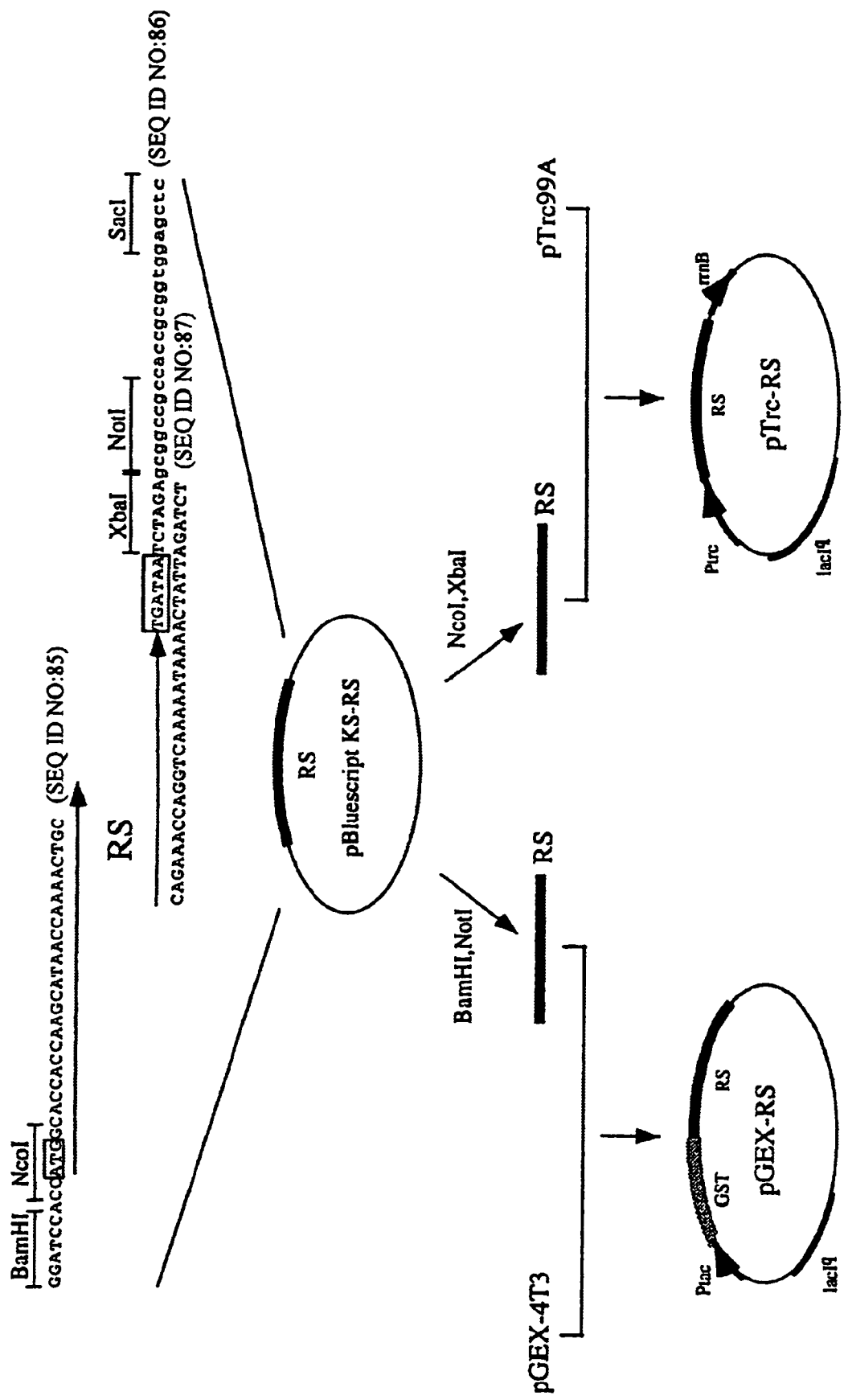
FIG. 1 shows the construction of plasmids used for the expression of a raffinose synthase gene in *Escherichia coli*. pBluescriptKS-RS™ is a plasmid containing the raffinose synthase gene cloned therein. RS represents the raffinose synthase gene, and the nucleotide sequences (SEQ ID NOS: 85-87) shown in the upper portion of this figure are those of both terminal portions of the raffinose synthase gene. A partial sequence represented by small letters is a nucleotide sequence derived from the vector pBluescriptII KS-™. Two boxed nucleotide sequences are the initiation codon (ATG) and termination codon (TGATAA) of the raffinose synthase gene, respectively. The recognition sites for several restriction endonucleases are shown above the nucleotide sequences. pGEX-RS and pTrc-RS are plasmids used for the expression of the raffinose synthase gene in *E. coli*. Ptac, Ptrc, GST, lacI$^q$, and rrnB represent tac promoter, trc promoter, glutathione-S-transferase gene, lactose repressor gene, and termination signal for the transcription of ribosomal RNA, respectively.

The gene engineering methods described below can be carried out according to ordinary methods, for example, as described in "Molecular Cloning: A Laboratory Manual 2nd edition" (1989), Cold Spring Harbor Laboratory Press, ISBN 0-87969-309-6; "Current Protocols In Molecular Biology" (1987), John Wiley & Sons, Inc. ISBN 0-471-50338-X; and "Current Protocols In Protein Science" (1995), John Wiley & Sons, Inc. ISBN 0-471-11184-8.

The term "raffinose synthase gene" as used herein refers to a gene having a nucleotide sequence coding for the amino acid sequence of a protein capable of producing raffinose by combining a D-galactosyl group through an α(1→6) bond with a hydroxyl group attached to the carbon atom at position 6 of a D-glucose residue in a sucrose molecule (hereinafter referred to simply as the present gene), and such a gene can be prepared, for example, from plants.

More specifically, the present gene can be prepared from dicotyledons such as leguminous plants (e.g., broad bean, soybean) and lamiaceous plants (e.g., Japanese artichoke) or from monocotyledons such as gramineous plants (e.g., corn). Specific examples of the present gene are a "raffinose synthase gene having a nucleotide sequence coding for a protein having the amino acid sequence of SEQ ID NO-2"; a "raffinose synthase gene having a nucleotide sequence coding for a protein having an amino acid sequence derived by deletion, replacement, modification or addition of one or several amino acids in the amino acid sequence of SEQ ID NO:2 and capable of producing raffinose by combining a D-galactosyl group through an α(1→6) bond with a hydroxyl group attached to the carbon atom at position 6 of a D-glucose residue in a sucrose molecule"; a "raffinose synthase gene having a nucleotide sequence coding for a protein having the amino acid sequence of SEQ ID NO:4"; a "raffinose synthase gene having a nucleotide sequence coding for a protein having an amino acid sequence derived by deletion, replacement, modification or addition of one or several amino acids in the amino acid sequence of SEQ ID NO:4, and capable of producing raffinose by combining a D-galactosyl group through an α(1→6) bond with a hydroxyl group attached to the carbon atom at position 6 of a D-glucose residue in a sucrose molecule"; a "raffinose synthase gene having a nucleotide sequence coding for the amino acid sequence of SEQ ID NO:6"; and a "raffinose synthase gene having a nucleotide sequence coding for the amino acid sequence of SEQ ID NO:8."

The present gene can be obtained, for example, by the following method.

The tissues of a leguminous plant such as broad bean (*Vicia faba*) or soybean (*Glycine Max*) are frozen in liquid nitrogen and ground physically with a mortar or other means into finely powdered tissue debris. From the tissue debris, RNA is extracted by an ordinary method. Commercially available RNA extraction kits can be utilized in the extraction. The whole RNA is separated from the RNA extract by ethanol precipitation. From the whole RNA separated, poly-A tailed RNA is fractionated by an ordinary method. Commercially available oligo-dT columns can be utilized in the fractionation. cDNA is synthesized from the fraction obtained (i.e., poly-A tailed RNA) by an ordinary method. Commercially available cDNA synthesis kits can be utilized in the synthesis.

For example, cDNA fragments of the "raffinose synthase gene having a nucleotide sequence coding for a protein having the amino acid sequence of SEQ ID NO:2" as the present gene can be obtained by PCR amplification using the broad bean-derived cDNA obtained above as a template and primers 1 to 3 (SEQ ID NOS:9-11) shown in list 1 below. The primers used therein can be designed and synthesized on the basis of the nucleotide sequence of SEQ ID NO:1, depending upon the purpose. For example, in order to amplify the open reading frame region of the "raffinose synthase gene having a nucleotide sequence coding for a protein having the amino acid sequence of SEQ ID NO:2," primers 1 to 4 (SEQ ID NOS:15-18) shown in list 2 below may be designed and synthesized.

In the same manner, cDNA fragments of the "raffinose synthase gene having a nucleotide sequence coding for a protein having the amino acid sequence of SEQ ID NO:4" can be obtained by PCR amplification with the soybean-derived cDNA obtained above as a template and, for example, primers 4 to 6 (SEQ ID NOS:12-14) shown in list 1 below. The primers used therein can be designed and synthesized on the basis of the nucleotide sequence of SEQ ID NO:3, depending upon the purpose. For example, in order to amplify the open reading frame region of the "raffinose synthase gene having a nucleotide sequence coding for a protein having the amino acid sequence of SEQ ID NO:4," primers 5 to 8 (SEQ ID NOS:19-22) shown in list 2 below may be designed and synthesized.

The amplified DNA fragments can be subcloned according to ordinary methods, for example, as described in "Molecular Cloning: A Laboratory Manual 2nd edition" (1989), Cold Spring Harbor Laboratory Press; and "Current Protocols In Molecular Biology" (1987), John Wiley & Sons, Inc. ISBN 0-471-50338-X. More specifically, cloning can be effected, for example, using a TA cloning kit (Invitrogen) and a plasmid vector such as pBluescript II (Stratagene). The nucleotide sequences of the DNA fragments cloned can be determined by the dideoxy terminating method, for example, as described by F. Sanger, S, Nicklen, A. R. Coulson, Proceedings of National Academy of Science U.S.A. (1977), 74, pp. 5463-5467. For example, ABI PRISM Dye Terminator Cycle Sequencing Ready Reaction Kit commercially available from Perkin-Elmer may preferably be used.

```
                             (List 1)

Primer 1: AATTTTCAAG CATAGCCAAG TTAACCACCT 30 mer (SEQ ID NO:9)

Primer 2: GCTCACAAGA TAATGATGTT AGTC 24 mer (SEQ ID NO:10)

Primer 3: ATACAAGTGA GGAACTTGAC CA 22 mer (SEQ ID NO:11)

Primer 4: CCAAACCATA GCAAACCTAA GCAC 24 mer (SEQ ID NO:12)
```

-continued

```
Primer 5: ACAACAGAAA AATATGACTC TTATTACT 28 mer (SEQ ID NO:13)

Primer 6: AAAAGAGAGT CAAACATCAT AGTATC 26 mer (SEQ ID NO:14)
```

(List 2)

```
Primer 1: ATGGCACCAC CAAGCATAAC CAAAACTGC 29 mer (SEQ ID NO:15)

Primer 2: ATGGCACCAC CAAGCATAAC CAAAACTGCA ACCCTCCAAG ACG 43 mer (SEQ ID NO:16)

Primer 3: TCAAAATAAA AACTGGACCA AAGAC 25 Mer (SEQ ID NO:17)

Primer 4: TCAAAATAAA AACTGGACCA AAGACAATGT 30 mer (SEQ ID NO:18)

Primer 5: ATGGCTCCAA GCATAAGCAA AACTG 25 mer (SEQ ID NO:19)

Primer 6: ATGGCTCCAA GCATAAGCAA AACTGTGGAA CT 32 mer (SEQ ID NO:20)

Primer 7: TCAAAATAAA AACTCAACCA TTGAC 25 mer (SEQ ID NO:21)

Primer 8: TCAAAATAAA AACTCAACCA TTGACAATTT TGAAGCACT 39 mer (SEQ ID NO:22)
```

The term "gene fragment" as used herein refers to a gene fragment having a partial nucleotide sequence of the present gene (hereinafter referred to simply as the present gene fragment). For example, it may be a gene fragment derived from a plant and having a partial nucleotide sequence of the gene having a nucleotide sequence coding for a protein capable of producing raffinose by combining a D-galactosyl group through an α(1→6) bond with a hydroxyl group attached to the carbon atom at position 6 of a D-glucose residue in a sucrose molecule. Specific examples of the present gene fragment are a gene fragment having a partial nucleotide sequence of the gene having a nucleotide sequence coding for the amino acid sequence of SEQ ID NO:2 and a gene fragment having a partial nucleotide sequence of the gene having a nucleotide sequence of SEQ ID NO:1, more specifically a gene fragment having a nucleotide sequence or a partial nucleotide sequence thereof, coding for any of the amino acid sequences (SEQ ID NOS:23-37) shown in list 3 below.

These gene fragments can be used as probes in the hybridization method or as primers in the PCR method. For the primers in the PCR method, it is generally preferred that the number of nucleotides is greater from a viewpoint that the specificity of annealing is ensured; it is, however, also preferred that the number of nucleotides is not so great from viewpoints that the primers themselves are liable to have a higher structure giving possible deterioration of the annealing efficiency and that complicated procedures are required in the purification after the synthesis. In usual cases, preferred is a gene fragment consisting of single-stranded DNA, wherein the number of nucleotides is in the range of from 15 to 50.

(List 3)

```
#1  Gly Ile Lys Phe Met Ser Ile Phe Arg Phe Lys Val Trp Trp Thr Thr His Trp Val
    Gly (SEQ ID NO:23)

#2  Ile Ile Asp Lys Phe Gly Trp Cys Thr Trp Asp Ala Phe
    Tyr (SEQ ID NQ:24)

#3  Gly Gly Cys Pro Pro Gly Phe Val Ile Ile Asp Asp Gly Trp
    Gln (SEQ ID NO:25)

#4  Thr Ser Ala Gly Glu Gln Met Pro Cys Arg Leu Val Lys Tyr Glu Glu
    Asn (SEQ ID NO:26)

#5  Val Tyr Val Trp His Ala Leu Cys Gly Tyr Trp Gly Gly Val Arg
    Pro (SEQ ID NO:27)

#6  Thr Met Glu Asp Leu Ala Val Asp Lys Ile Val Glu Asn Gly Val Gly Leu Val Pro
    Pro (SEQ ID NQ:28)

#7  Gly Leu His Ser His Leu Glu Ser Ala Gly Ile Asp Gly Val Lys Val Asp Val Ile
    His Leu Leu Glu (SEQ ID NQ:29)

#8  Gly Gly Arg Val Glu Leu Ala Arg Ala Tyr Tyr Lys Ala
    Leu (SEQ ID NQ:30)

#9  Val Lys Lys His Phe Lys Gly Asn Gly Val Ile
    Ala (SEQ ID NO:31)

#10 Glu His Cys Asn Asp Phe Phe Leu Leu Gly Thr Glu Ala Ile Ser Leu Gly
    Arg Val Gly Asp Asp Phe Trp Cys Ser Asp Pro Ser Gly Asp
    Pro Asn Gly Thr Tyr Trp Leu Gln Gly Cys His Met Val His
```

-continued

Cys (SEQ ID NO:32)

11 Ala Tyr Asn Ser Leu Trp Met Gly Asn Phe Ile Gln Pro Asp Trp Asp Met
    Phe Gln Ser Thr His Pro Cys Ala Glu Phe His Ala Ala Ser
    Arg Ala Ile Ser Gly Gly Pro Ile Tyr Val Ser
    Asp (SEQ ID NO:33)

12 Leu Pro Asp Gly Ser Ile Leu Arg Cys (SEQ ID NO:34)

13 Ala Leu Pro Thr Arg Asp Cys Leu Phe Glu Asp Pro Leu His Asn Gly Lys
    Thr Met Leu Lys Ile Trp Asn (SEQ ID NO:35)

14 Gly Val Lcu Gly Lcu Phe Asn Cys Gln Gly Gly Gly
    Trp (SEQ ID NO:36)

15 Phe Ala Pro Ile Gly Leu Val Asn Met (SEQ ID NO:37)

The present gene fragment is labeled, and then used as a probe in the hybridization method and hybridized to organism-derived DNA, so that a DNA fragment having the probe specifically bound thereto can be detected. Thus, from an organism-derived gene library, a raffinose synthase gene having a nucleotide sequence coding for the amino acid sequence of an enzyme capable of producing raffinose by combining a D-galactosyl group through an α(1→6) bond with a hydroxyl group attached to the carbon atom at position 6 of a D-glucose residue in a sucrose molecule; or a gene fragment having a partial nucleotide sequence thereof, can be detected (hereinafter referred to simply as the present detection method).

As the organism-derived DNA, for example, a cDNA library or a genomic DNA library of a desired plant can be used. The gene library may also be a commercially available gene library as such or a library prepared according to an ordinary library preparation method, for example, as described in "Molecular Cloning: A Laboratory Manual 2nd edition" (1989), Cold Spring Harbor Laboratory Press; "Current Protocols In Molecular Biology" (1987), John Wiley & Sons, Inc. ISBN 0-471-50338-X.

As the hybridization method, plaque hybridization or colony hybridization can be employed, depending upon the kind of vector used in the preparation of a library. More specifically, when a library to be used is constructed with a phage vector, a suitable host microorganism is mixed with the phage under infectible conditions, which is further mixed with a soft agar medium, and the mixture is plated on an agar medium. Thereafter, a culture is grown at 37° C. until a plaque of an appropriate size appears. When a library to be used is constructed with a plasmid vector, the plasmid is transformed in a suitable host microorganism to form a transformant. The transformant obtained is diluted to a suitable concentration, and the dilution is plated on an agar medium, after which a culture is grown at 37° C. until a colony of an appropriate size appears.

In either case of the above libraries, a membrane filter is placed on the surface of the agar medium after the cultivation, so that the phage or transformant is transferred to the membrane. This membrane is denatured with an alkali, followed by neutralization, and for example, when a nylon membrane is used, the membrane is irradiated with ultraviolet light, so that DNA is fixed on the membrane. This membrane is then subjected to hybridization with the present gene fragment labeled by an ordinary method as a probe. For this method, reference may be made, for example, to D. M. Glover ed., "DNA cloning, a practical approach" IRL PRESS (1985), ISBN 0-947946-18-7. There are various reagents and temperature conditions to be used in the hybridization; for example, prehybridization is carried out by the addition of 6×SSC (0.9 M NaCl, 0.09 M citric acid), 0.1-1% SDS, 100 μ/ml denatured salmon sperm DNA, and incubation at 65° C. for 1 hour. The present gene fragment labeled is then added as a probe, and mixed. Hybridization is carried out at 42-68° C. for 4 to 16 hours. The membrane is washed with 2×SSC, 0.1-1% SDS, further rinsed with 0.2×SSC, 0-0.1% SDS, and then dried. The membrane is analyzed, for example, by autoradiography or other techniques, to detect the position of the probe on the membrane and thereby detect the position of DNA having a nucleotide sequence homologous to that of the probe used. Thus, the present gene or the present gene fragment can be detected. The clone corresponding to the position of DNA thus detected on the membrane is identified on the original agar medium, and the positive clone is selected, so that the clone having the DNA can be isolated. The same procedures of detection are repeated to purify the clone having the DNA.

Other detection methods can also be used, for example, GENE TRAPPER cDNA Positive Selection System Kit commercially available from Gibco BRL. In this method, a single-stranded DNA library is hybridized with the present gene fragment biotinylated (i.e., probe), followed by the addition of streptoavidin-bound magnet beads and mixing. From the mixture, the streptoavidin-bound magnetic beads are collected with a magnet, so that single-stranded DNA having a nucleotide sequence homologous to that of the probe used, which has been bound to these beads through the present gene fragment, biotin and streptoavidin, is collected and detected. Thus, the present gene or the present gene fragment can be detected. The single-stranded DNA collected can be changed into a double-strand form by treatment with a suitable DNA polymerase using a suitable oligonucleotide as a primer.

The present detection method may also be used in the analysis of a plant. More specifically, plant genomic DNA is prepared according to an ordinary method, for example, as described in "Cloning and Sequence (Plant Biotechnology Experiment Manual)" complied under the supervision of Itaru Watanabe, edited by Masahiro Sugiura, published by Noson Bunka-sha, Tokyo (1989). The plant genomic DNA is digested with several kinds of suitable restriction endonucleases, followed by electrophoresis, and the electrophoresed DNA is blotted on a filter according to an ordinary method. This filter is subjected to hybridization with a probe prepared from the present gene fragment by an ordinary method, and DNA fragments to which the probe hybridizes are detected. The DNA fragments detected are compared in length between different varieties of a specified plant species. The differences in length make possible the analysis of differences in phenotypic characteristics accompanied with the expression of raffinose family oligosaccharides between these varieties.

Furthermore, when the DNA fragments detected by the above method are compared in length between the gene recombinant plant and the non-gene recombinant plant of the same variety, the former plant can be discriminated from the latter plant by the detection of hybridizing bands greater in number or higher in concentration for the former plant than for the latter plant. This method can be carried out according to the RFLP (restriction fragment length polymorphism) method, for example, as described in "Plant PCR Experiment Protocols" complied under the supervision of Ko Shimamoto and Takuji Sasaki, published by Shujun-sha, Tokyo (1995), ISBN 4-87962-144-7, pp. 90-94.

The PCR method using a primer having the nucleotide sequence of the present gene fragment makes it possible to amplify from organism-derived DNA, a raffinose synthase gene having a nucleotide sequence coding for the amino acid sequence of an enzyme capable of producing raffinose by combining a D-galactosyl group through an α(1→6) bond with a hydroxyl group attached to the carbon atom at position 6 of a D-glucose residue in a sucrose molecule; or a gene fragment having a partial nucleotide sequence thereof (hereinafter referred to simply as the present amplification method).

More specifically, for example, an oligonucleotide having 15 to 50 nucleotides in the nucleotide sequence of the present gene fragment at the 3'-terminus is chemically synthesized by an ordinary synthesis method. Based on the codon table below, showing the correspondence of amino acids encoded in nucleotide sequences, a mixed primer can also be synthesized so that a residue at a specified position in the primer is changed to a mixture of several bases, depending upon the variation of codons which can encode a certain amino acid.

CODON TABLE

| Phe | UUU | Ser | UCU | Tyr | UAU | Cys | UGU |
|---|---|---|---|---|---|---|---|
|  | UUC |  | UCC |  | UAC |  | UGC |
| Leu | UUA |  | UCA | Stop | UAA | Stop | UGA |
|  | UUG |  | UCG |  | UAG | Trp | UGG |
|  | CUU | Pro | CCU | His | CAU | Arg | CGU |
|  | CUC |  | CCC |  | CAC |  | CGC |
|  | CUA |  | CCA | Gln | CAA |  | CGA |
|  | CUG |  | CCG |  | CAG |  | CGG |
| Ile | AUU | Thr | ACU | Asn | AAU | Ser | AGA |
|  | AUC |  | ACC |  | AAC |  | AGG |
|  | AUA |  | ACA | Lys | AAA | Arg | CGU |
| Met | AUG |  | ACG |  | AAG |  | GGC |
| Val | GGU | Ala | GCU | Asp | GAU | Gly | GGU |
|  | GUC |  | GCC |  | GAC |  | GGC |
|  | GUA |  | GCA | Glu | GAA |  | GGA |
|  | GUG |  | GCG |  | GAG |  | GGG |

Furthermore, a base capable of forming a pair with plural kinds of bases, such as inosine, can also be used instead of the above mixture of several bases. More specifically, for example, primers having nucleotide sequences (SEQ ID NOS:38-47) as shown in list 4 can be used. In this context, an oligonucleotide having the same nucleotide sequence as the coding strand of the present gene consisting of double-stranded DNA is designated "sense primer," and an oligonucleotide having a nucleotide sequence complementary to the coding strand, "antisense primer."

A sense primer having the same nucleotide sequence as present on the 5'-upstream side in the coding strand of a raffinose synthase gene or a gene fragment having a partial nucleotide sequence thereof to be amplified, and an antisense primer having a nucleotide sequence complementary to the nucleotide sequence on the 3'-downstream side in this coding strand, are used in combination for PCR reaction to amplify a DNA fragment, for example, with a gene library, genomic DNA or cDNA as a template. At this time, the amplification of a DNA fragment can be confirmed by an ordinary method with electrophoresis. For the DNA fragment amplified, its restriction endonuclease map is constructed or its nucleotide sequence is determined by an ordinary method, so that the present gene or the present gene fragment can be identified. As the gene library used herein, for example, a cDNA library or a genomic cDNA library of a desired plant can be used. For the plant gene library, a commercially available library derived from plant can be used as such; or a library prepared according to an ordinary library preparation method, for example, as described in "Molecular Cloning: A Laboratory Manual 2nd edition" (1989), Cold Spring Harbor laboratory Press or "Current Protocols in Molecular Biology" (1987), John Wiley & Sons, Inc., ISBN 0-471-50338-X, can also be used. As the genomic DNA or cDNA used in the present amplification method, for example, cDNA or genomic cDNA prepared from a desired plant can be used.

More specifically, for example, a primer designed on the amino acid sequence of SEQ ID NO:2 is used for the present amplification method with cDNA derived from Japanese artichoke, which is a lamiaceous plant, as a template, so that a raffinose synthase gene fragment having the nucleotide sequence of SEQ ID NO:5 can be amplified. Furthermore, for example, a primer designed on the amino acid sequence of SEQ ID NO:2 is used for the present amplification method with cDNA derived from corn, which is a gramineous plant, as a template, so that a raffinose synthase gene fragment having the nucleotide sequence of SEQ ID NO:7 can be amplified.

```
                        (List 4)

1-F   32 mer
                    TTIAAIGTITGGTGGACIACICAITGGGTIGG (SEQ ID NO:38)
              2-F   41 mer
                    ATIATIGAIAAITTIGGITGGTGIACITGGGAIGCITTITA (SEQ ID NO:39)
              2-RV  41 mer
                    TAIAAIGCITCCCAIGTICACCAICCIAAITTITCIATIAT (SEQ ID NO:40)
              3-F   44 mer
                    GGIGGITGICCICCIGGITTIGTIATIATIGAIGAIGGITGGCA (SF0 ID NO:41)
              3-RV  44 mer
                    TGCCAICCITCITCIATIATIACIAAICCIGGIGGICAICCICC (SEQ ID NO:42)
              4-F   32 mer
                    AAIAAICAITTIAAIGGIAAIGGIGTIATIGC (SEQ ID NO:43)
```

-continued

4-RV 32 mer
    GCIATIACICCITTICCITTIAAITGITTITT (SEQ ID NO:44)
5-F  38 mer
    TGGATGGGIAAITTIATICAICCIGAITGGGAIATGTT (SEQ ID NO:45)
5-RV 38 mer
    AACATITCCCAITCIGGITGIATIAAITTICCCATCCA (SEQ ID NO:46)
6-RV 27 mer
    CATITTIACIA(AG)ICCIATIGGIGCIAA (SEQ ID NO:47)

The present amplification method can also be utilized for the analysis of a plant gene. More specifically, for example, plant genomic DNA prepared from different varieties of a specified plant species is used as a template for the present amplification method to amplify a DNA fragment. The DNA fragment amplified is mixed with a solution of formaldehyde, which is denatured by heating at 85° C. for 5 minutes, followed by rapid cooling on ice. This sample is subjected to electrophoresis, for example, on a 6% polyacrylamide gel containing 0% or 10% glycerol. In this electrophoresis, a commercially available electrophoresis apparatus for SSCP (single strand conformation polymorphism) can be used, and electrophoresis is carried out, while the gel is kept at a constant temperature, e.g., 5° C., 25° C. or 37° C. From the electrophoresed gel, a DNA fragment is detected, for example, by a method such as silver staining method with commercially available reagents.

From the differences of behavior between the varieties in the electrophoresis of the DNA fragment detected, a mutation in the raffinose synthase gene is detected, and an analysis is carried out for differences caused by the mutation in phenotypic characteristics accompanied with the expression of raffinose family oligosaccharides. This method can be carried out according to the SSCP method, for example, as described in "Plant PCR Experiment Protocols" complied under the supervision of Ko Shimamoto and Takuji Sasaki, published by Shujun-sha, Tokyo (1995), ISBN 4-87962-144-7, pp. 141-146.

The present detection method or the present amplification method as described above can also be used for identifying a raffinose synthase gene or a gene fragment having a partial nucleotide sequence thereof and then isolating and purifying the identified gene or gene fragment thereof to obtain the present gene (hereinafter referred to simply as the present gene acquisition method).

The present gene or the present gene fragment can be obtained, for example, by detecting a probe consisting of the present gene fragment hybridized to DNA in the organism-derived gene library by the present detection method as described above to identify DNA having a nucleotide sequence homologous with the probe used; purifying a clone carrying the DNA; and isolating and purifying plasmid or phage DNA from the clone. When the DNA thus obtained is a gene fragment having a partial nucleotide sequence of the raffinose synthase gene, further screening of the gene library by the present gene detection method using the DNA as a probe gives the present gene in full length.

The present gene or the present gene fragment can be identified, for example, by effecting polymerase chain reaction using a primer having the nucleotide sequence of the present gene fragment to amplify a DNA fragment from the organism-derived DNA by the present amplification method as described above; and then constructing a restriction endonuclease map or determining a nucleotide sequence for the amplified DNA fragment. Based on the nucleotide sequence of the gene fragment obtained, an antisense primer is synthesized for the analysis of 5'-terminal sequences, and a sense primer is synthesized for the analysis of 3'-terminal sequences. The nucleotide sequence of the present gene in full length can be determined by the RACE method using these primers and a commercially available kit, e.g., Marathon Kit of Clontech. The present gene in full length can be obtained by synthesizing new primers based on both terminal sequences in the nucleotide sequence thus determined and effecting polymerase chain reaction again.

The present gene acquisition method as described above makes it possible to obtain raffinose synthase genes as the present gene from various organisms. For example, a gene coding for a raffinose synthase having an amino acid sequence that has about 50% or higher homology, in the region corresponding to the length of 400 or more amino acids, with the amino acid sequence of SEQ ID NO:2, and capable of producing raffinose by combining a D-galactosyl group through an α(1→6) bond with a hydroxyl group attached to the carbon atom at position 6 of a D-glucose residue in a sucrose molecule. More specifically, for example, a raffinose synthase gene having the nucleotide sequence of SEQ ID NO:3 can be obtained by amplifying and identifying a DNA fragment containing a gene fragment having a partial nucleotide sequence of the raffinose synthase gene by the present amplification method using primers designed from the amino acid sequence of SEQ ID NO:2 and soybean cDNA as a template; isolating and purifying the identified DNA fragment, followed by the above procedures to obtain a full-length gene containing the DNA fragment.

A chimera gene comprising the present gene and a promoter linked thereto (hereinafter referred to simply as the present chimera gene) can be constructed.

The promoter to be used is not particularly limited, so long as it is functionable in a host organism to be transformed. The promoter may include, for example, synthetic promoters functionable in *Escherichia coli*, such as *E. coli* lactose operon promoter, *E. coli* tryptophan operon promoter and tac promoter; yeast alcohol dehydrogenase gene (ADH) promoter, adenovirus major late (Ad.ML) promoter, SV40 early promoter, and baculovirus promoter.

When the host organism is a plant or a cell thereof, the promoter may include, for example, T-DNA derived constitutive promoters such as nopaline synthase gene (NOS) promoter and octopine synthase gene (OCS) promoter; plant virus-derived promoters such as cauliflower mosaic virus (CaMV) derived 19S and 35S promoter; derived promoters such as phenylalanine ammonia-lyase (PAL) gene promoter, chalcone synthase (CHS) gene promoter and pathogenesis-related protein (PR) gene promoter. Furthermore, vector pSUM-GY1 (see JP-A 06-189777/1994) can also be used, which has a promoter giving specific expression in a specified plant tissue, e.g., a promoter of soybean-derived seed storage protein glycinin gene. The use of a chimera gene constructed so as to have such a promoter makes it possible to increase or decrease the content of raffinose family oligosaccharides in a specified tissue of a plant.

The present chimera gene is then introduced into a host organism according to an ordinary gene engineering method to give a transformant. If necessary, the present chimera gene may be used in the form of a plasmid, depending upon the transformation method for introducing the gene into the host organism. Furthermore, the present chimera gene may contain a terminator. In this case, it is generally preferred that the chimera gene is constructed so as to have a terminator downstream the raffinose synthase gene. The terminator to be used is not particularly limited, so long as it is functionable in a host organism to be transformed. For example, when the host organism is a plant or a cell thereof, the terminator may include, for example, T-DNA derived constitutive terminators such as nopaline synthase gene (NOS) terminator; and plant derived terminators such as terminators of allium virus GV1 or GV2.

If necessary, the present gene may be used in the form of a plasmid. For example, when the host organism is a microorganism, the plasmid constructed is introduced into the microorganism by an ordinary means, for example, as described in "Molecular Cloning: A Laboratory Manual 2nd edition" (1989), Cold Spring Harbor laboratory Press or "Current Protocols in Molecular Biology" (1987), John Wiley & Sons, Inc., ISBN 0-471-50338-X. The microorganism thus transformed is selected with a marker such as antibiotic resistance or auxotrophy. When the host organism is a plant, the plasmid constructed is introduced into a plant cell by an ordinary means such as infection with *Agrobacterium* (see JP-B 2-58917/1990 and JP-A 60-70080/1985), electroporation into protoplasts (see JP-A 60-251887/1985 and JP-B 5-68575/1993) or particle gun method (see JP-A 5-508316/1993 and JP-A 63-258525/1988). The plant cell transformed by the introduction of a plasmid is selected with an antibiotic such as kanamycin or hygromycin. From the plant cell thus transformed, a transformed plant can be regenerated by an ordinary plant cell cultivation method, for example, as described in "Plant Gene Manipulation Manual (How to Produce Transgenic Plants)" written by Uchimiya, 1990, Kodansha Scientific (ISBN 4-06153513-7), pp. 27-55. Furthermore, the collection of seeds from the transformed plant also makes it possible to prolify the transformed plant. In addition, crossing between the transformed plant obtained and the non-transformed plant makes it possible to produce progenic plants with the character of the transformed plant.

The content of raffinose family oligosaccharides can be changed by introducing the present gene into a host organism or a cell thereof, and modifying the metabolism in the host organism or the cell thereof. As such a method, for example, there can be used a method for metabolic modification to increase the amount of raffinose family oligosaccharides in a host organism or a cell thereof by constructing the present chimera gene comprising the present gene and a promoter linked thereto, in which case the present gene is linked to the promoter in an original direction suitable for transcription, translation, and expression as a protein, and then introducing the present chimera gene into the host organism or the cell thereof; or a method for metabolic modification to decrease the amount of raffinose family oligosaccharides in a host organism or a cell thereof by constructing the present chimera gene comprising the present gene and a promoter linked thereto, in which case the present gene is linked to a promoter in a reverse direction unsuitable for translation and expression as a protein, and then introducing the present chimera gene into the host organism or the cell thereof.

The term "raffinose synthase protein" as used herein refers to a protein encoded in the present gene (hereinafter referred to simply to the present protein). For example, it may include an enzyme protein having the amino acid sequence of SEQ ID NO:2 or SEQ ID NO:4, or having an amino acid sequence derived by deletion, replacement, modification or addition of one or several amino acids in the amino acid sequence of SEQ ID NO:2 or SEQ ID NO:4; and capable of producing raffinose by combining a D-galactosyl group through an $\alpha(1\rightarrow6)$ bond with a hydroxyl group attached to the carbon atom at position 6 of a D-glucose residue in a sucrose molecule.

Specific examples of the present protein are an enzyme protein having the amino acid sequence of SEQ ID NO:2 (799 amino acids; molecular weight, 89 kDa) and an enzyme protein having the amino acid of SEQ ID NO:4 (781 amino acids; molecular weight, 87 kDa).

The present protein, although it can be prepared, for example, from leguminous plants such as broad bean (*Vicia faba*), by an ordinary biochemical method such as $(NH_4)_2SO_4$ precipitation, ion exchange column, hydrophobic column, hydroxyapatite column or gel filtration column, can also be prepared from the host organism transformed with the present plasmid, or a cell thereof. More specifically, for example, using GST Gene Fusion Vectors Kit of Pharmacia, the present gene is inserted into an expression vector plasmid attached to the kit. The resulting vector plasmid is introduced into a microorganism such as *E. coli* according to an ordinary gene engineering method. A culture of the transformant obtained is grown on a medium with the addition of IPTG (isopropylthio-β-D-galactoside), so that the present protein can be expressed and derived as a fused protein in the culture. The fused protein expressed and induced can be isolated and purified by an ordinary method such as disruption of bacterial cells, column operation or SDS-PAGE electrophoresis. The digestion of the fused protein with a protease such as thrombin or blood coagulation factor Xa gives the present protein. This may preferably be made, for example, according to the method described in "Current Protocols In Protein Science" (1995), John Wiley & Sons, Inc. ISBN 0-471-11184-8. The activity of the present protein can be measured, for example, by the method described in L. Lehle and W. Tanner, Eur. J. Biochem., 38, 103-110 (1973).

An anti-raffinose synthase antibody capable of binding to a raffinose synthase protein (hereinafter referred to simply as the present antibody) can be produced by an ordinary immunological method using the present protein prepared above, as an antigen. More specifically, the present antibody can be produced, for example, according to the method described in Ed Harlow and David Lane, "Antibodies: A Laboratory Manual" (1988), Cold Spring Harbor Laboratory Press, ISBN 0-87969-314-2.

The present protein can be detected by treating test proteins with the present antibody and detecting a protein having the present antibody bound specifically thereto. Such a detection method can be carried out according to an immunological technique such as Western blot method or enzyme-linked immunosorbent assay (ELISA), for example, as described in Ed Harlow and David Lane, "Antibodies: A Laboratory Manual" (1988), Cold Spring Harbor Laboratory Press.

The Western blot method is carried out, for example, as follows: Proteins are extracted from a plant, for example, according to the method described in Methods in Enzymology, volume 182, "Guide to Protein Purification," pp. 174-193, ISBN 9-12-182083-1. The composition of an extraction buffer can suitably be changed depending upon the plant tissue used. The proteins extracted are electrophoresed according to an ordinary SDS-PAGE method. The proteins electrophoresed in the gel are transferred to a membrane by Western blotting with an ordinary electrical method. More specifically, for example, the gel is immersed in a transfer buffer (25 mM Tris, 192 mM glycine, 20% methanol) for 10 minutes, and then placed onto a PVDF membrane cut into the same size as that of the gel. The gel together with the membrane is set in a commercially available transfer apparatus of the semi-dry type. Blotting is carried out at a constant current of 0.8 to 2 mA/cm$^2$ for 45 minutes to 1 hour. The proteins transferred to the membrane can be detected immunologically with a kit for Western blot detection using a primary antibody, and a secondary antibody or protein A, which has been labeled with alkaline phosphatase or horseradish peroxidase. At this time, the present protein on the membrane can be detected by the use of the present antibody as a primary antibody.

In the ELISA method, for example, the property of proteins binding to the surface of a 96-well ELISA plate made of a resin is utilized in principle for the immunological detection of an antigen finally bound to the surface of the ELISA plate. The test proteins are added as a solution and bound to an ELISA plate, followed by blocking, for example, by the addition of PBS containing a protein such as 5% bovine serum albumin. Thereafter, the well is washed with PBS, to which a solution containing the present antibody is added to effect the reaction. After the well is washed, a solution containing a secondary antibody labeled with alkaline phosphatase or horseradish peroxidase is further added to the well, followed by washing. Finally, a substrate solution for detection is added to the well, and the color development of the substrate is detected with an ELISA reader.

In another method, the present antibody is added and bound to an ELISA plate, followed by blocking, for example, by the addition of PBS containing a protein such as 5% bovine serum albumin. The test proteins are then added as a solution, and an antigen contained in the test proteins is bound to the present antibody that has been bound to the plate, followed by washing, and the present antibody is further added to the well. The present antibody used at this time is preferably one prepared from an animal species different from that used for the preparation of the present antibody used first. A solution containing a secondary antibody labeled with alkaline phosphatase or horseradish peroxidase is then added to the well, followed by washing. The secondary antibody used at this time must have the property of binding to the present antibody added later. Finally, a substrate solution for detection is added, and the color development is detected with an ELISA reader.

EXAMPLES

The present invention will be further illustrated by the following examples; however, the present invention is not limited to these example in any way whatsoever.

Example 1

Purification of Galactinol

About 250 ml of sugar beet blackstrap molasses was five-fold diluted with methanol. The dilution was centrifuged at 21,400×g for 15 minutes at room temperature to remove insoluble matter. The supernatant obtained was transferred into a 2-liter Erlenmeyer flask, to which isopropanol at a half volume was added portionwise with stirring. The flask was left at room temperature for a while until the resulting precipitate adhered to the wall of the flask. The supernatant was then discarded by decantation. To the precipitate was added 500 ml of ethanol, and the mixture was washed with stirring with a rotary shaker. The washing was further repeated several times. The washed precipitate was scraped off from the wall of the flask, followed by air drying on a filter paper. The air-dried precipitate (dry powder) was dissolved in purified water to about 40% (w/v). To this solution was added AG501-X8(D) of BioRad, followed by stirring. This operation was repeated until the color of the solution became almost unobserved. The resulting solution was treated with a Sep-Pak™ QMA column of Millipore, and further pretreated with Sep-Pak™ CM Sep-Pak™ C18 and Sep-Pak™ Silica columns of Millipore. The resulting solution was loaded at a volume of 5 ml onto a column of Wako-gel™ LP40C18 (Wako Pure Chemical Industries, 2.6 cm×85 cm), and eluted with purified water. The sugar content of the eluate was measured with a portable sugar refractometer, and the sugar composition was analyzed by high performance liquid chromatography (HPLC) with a Sugar-pak™ Na (7.8 mm×300 mm) column of Millipore. The detection of sugars was carried out with model 410 Differential Refractometer of Waters. The eluate containing galactinol was lyophilized, and the resulting lyophilized powder was dissolved in 5 ml of purified water. The solution was loaded onto a column of TOYOPEARL™ HW40(S) (Toso, 2.6 cm×90 cm), and eluted with purified water. The eluate was analyzed in the same manner as described above, so that purified galactinol was obtained.

The galactinol obtained was kept at 25° C. for 40 minutes in the reaction mixture that came to contain 80 mM phosphate buffer (pH 6.5), 2 mg/ml galactinol, and 8.3 U α-galactosidase (Boehringer Mannheim, *E. coli* overproducer 662038). The reaction mixture was extracted with chloroform, and the water layer was analyzed by HPLC. The resulting galactinol was confirmed to be hydrolyzed into galactose and myo-inositol.

Example 2

Measurement of Raffinose Synthase Activity

The raffinose synthase activity was measured under the following conditions according to the description of L. Lehle and W. Tanner, Eur. J. Biochem., 38, 103-110 (1973).

First, 2 μl of a sample to be used in the measurement of activity was added to 18 μl of the reaction mixture that came to contain 100 mM Tris-HCl (pH 7.4), 5 mM DTT (dithiothreitol), 0.01% BSA, 200 μM sucrose, 5 mM galactinol, 740 KBq/ml (31.7 μM) [$^{14}$C] sucrose, and the reaction mixture was kept at 37° C. for 3 to 20 hours. After the reaction, 30 μl of ethanol was added to the reaction mixture, followed by stirring and centrifugation at 15,000 rpm for 5 minutes. The supernatant was spotted at a volume of 5 μl on an BPTLC plate of cellulose for thin layer chromatography (Merck, 10 cm×20 cm), and developed with n-butanol:pyridine:water:acetic acid=60:40:30:3. The developed plate was dried and then quantitatively analyzed with an imaging analyzer (Fuji Photographic Film, FUJIX Bio Imaging Analyzer BAS-2000II) for the determination of [$^{14}$C] raffinose produced.

Example 3

Purification of Raffinose Synthase

The purification of raffinose synthase from broad bean was carried out as follows: For each purified protein solution, proteins present in the protein solution were analyzed by SDS-PAGE (Daiichi Kagaku Yakuhin), and the enzyme activity thereof was measured according to the method described in Example 2.

First, 300 g of immature seeds of broad bean (Nintoku Issun) stored at −80° C. was thawed and then peeled. The peeled seeds were put in 600 ml of 100 mM Tris-HCl (pH 7.4), 5 mM DTT (dithiothreitol), 1 mM EDTA, 1 mM PMSF (phenylmethylsulfonyl fluoride) and 1 mM benzamide, and ground on ice with a mortar. The ground material was centrifuged at 21,400×g for 50 minutes at 4° C. To the resulting supernatant was added 10% polyethylene imine (pH 8.0) at a 1/20 volume. The mixture was stirred at 4° C. for 15 minutes, and centrifuged at 15,700×g for 20 minutes at 4° C. To the resulting supernatant was added 196 g/l of $(NH_4)_2SO_4$ with stirring. The mixture was stirred in ice for 30 minutes, and centrifuged at 15,700×g for 20 minutes at 4° C. To the resulting supernatant was further added 142 g/l of $(NH_4)_2SO_4$ with stirring. After the stirring in ice for 30 minutes, the mixture was centrifuged at 15,700×g for 20 minutes at 4° C. The resulting precipitate was dissolved in 50 ml of 100 mM Tris-HCl (pH 7.4) and 5 mM DTT (dithiothreitol), and the solution was dialyzed against 20 mM Tris-HCl (pH 7.4), 1 mM DTT (dithiothreitol) and 1 mM EDTA at 4° C. overnight. After the dialysis, the suspension was centrifuged at 70,000×g for 60 minutes at 4° C. To the resulting supernatant was added 1 mM benzamidine.HCl, 5 mM ε-amino-n-caproic acid, 1 µg/ml antipain, 1 µg/ml leupeptin and 10 mM EGTA, and 2 M KCl was further added portionwise at a 1/40 volume. The mixture was loaded onto a column of DEAE-Sephacel™ (Pharmacia, 2.5 cm×21.5 cm) equilibrated with 0.05 M KCl, 20 mM Tris-HCl (pH 7.4), 1 mM DTT (dithiothreitol) and 1 mM EDTA, and the adsorbed proteins were eluted with a gradient of 0.05 to 0.5 M KCl. The purification steps up to this stage were repeated three times, and fractions having raffinose synthase activity were combined and then purified as follows:

To the eluted fraction having raffinose synthase activity was added portionwise saturated $(NH_4)_2SO_4$ at a 1/4 volume. The solution was loaded onto a column of Phenyl-Sepharose (Pharmacia, 2.5 cm×10.2 cm) equilibrated with 20% saturated $(NH_4)_2SO_4$, mM Tris-HCl (pH 7.4), 1 mM DTT (dithiothreitol) and 1 mM EDTA, and the adsorbed proteins were eluted with a gradient of 20% to 0% $(NH_4)_2SO_4$. The resulting active fraction was diluted by the addition of 0.01 M potassium phosphate buffer (pH 7.5) at a 2-fold volume. The diluted solution was loaded onto a column of Econo-Pac™ 10DG (BioRad, 5 ml) previously equilibrated with 0.01 M potassium phosphate buffer (pH 7.5) and 2 mM DTT (dithiothreitol), and the adsorbed proteins were eluted with a gradient of 0.01 to 0.5 M potassium phosphate buffer (pH 7.5) and 2 mM DTT (dithiothreitol). The active fraction obtained at this stage was found to have been purified up to 6500-fold or higher specific activity. Part of the resulting purified protein solution having raffinose synthase activity was loaded onto a column of Superdex™ 200 (Pharmacia, 1.6 cm×60 cm) equilibrated with 0.2 M KCl, 20 mM Tris-HCl (pH 7.4), 1 mM DTT (dithiothreitol) and 1 mM EDTA. The purified proteins thus separated were subjected to SDS-PAGE, and the raffinose synthase activity was measured. A protein band having raffinose synthase activity was identified as having a molecular weight of about 90 kDa on the SDS-PAGE.

Example 4

Analysis of Partial Amino Acid Sequence of Raffinose Synthase

To about 1 ml of the purified protein solution, which had been purified with a column of Econo-Pac 10DG (BioRad, 5 ml) in Example 3, was added 100% TCA at a 1/9 volume, and the mixture was left on ice for 30 minutes. After centrifugation at 10,000×g for 15 minutes, the resulting precipitate was suspended in 500 µl of cold acetone (−20° C.), followed by further centrifugation. This acetone washing was repeated, and the collected precipitate was dried and then dissolved in 200 µl of SDS-sample buffer, followed by SDS-PAGE. CBB staining was effected for the electrophoresed gel, from which the band of a raffinose synthase protein was cut out.

To the gel thus taken was added 1 ml of 50% acetonitrile and 0.2 M ammonium carbonate (pH 8.9), and washing was continued with stirring at room temperature for 20 minutes. The gel was washed once again in the same manner, and dried under reduced pressure to an extent giving a volume reduction. To this gel was 1 ml of 0.02% Tween-20 and 0.2 M ammonium carbonate (pH 8.9), and the mixture was stirred at room temperature for 15 minutes. After removal of the solution, 400 µl of 8 M urea and 0.4 M $NH_4HCO_3$ was added, to which 40 µl of 45 mM DTT (dithiothreitol) was further added, and the mixture was left at 50° C. for 20 minutes. After complete return to room temperature, 4 µl of 1 M iodoacetic acid was added, and the mixture was stirred in the dark at room temperature for 20 minutes. After removal of the solution, 1 ml of purified water was added, and the mixture was stirred at room temperature for 5 minutes, followed by washing. After further two washings, 1 ml of 50% acetonitrile and 0.2 M ammonium carbonate (pH 8.9) was added, and the mixture was stirred at room temperature for 15 minutes. The same treatment was repeated once again, after which the solution was removed, and the gel was dried under reduced pressure to an extent giving a volume reduction.

To this gel was added a solution of *Achromobacter* Protease I (Takara, Residue-specific Protease Kit) at a volume of 100 µl. Further added was 0.02% Tween-20 and 0.2 M ammonium carbonate (pH 8.9) to an extent that the gel was not exposed from the surface of the solution, and the mixture was left at 37° C. for 42 hours. Further added was 500 µl of 0.09% TFA and 70% acetonitrile, and the mixture was stirred at room temperature for 30 minutes. The resulting mixture as contained in a sample tube was floated in an ultrasonic bath, followed by ultrasonic treatment (BRANSON, 60 W output power) for 5 minutes. The tube and contents thus treated were centrifuged, and the resulting extract was collected in another silicone-coated sample tube. On the other hand, 500 µl of 0.09% TFA and 70% acetonitrile was added again to the precipitate, followed by repeated extraction in the same manner as described above. The resulting extracts were combined and then concentrated under reduced pressure to an extent giving a solution remained at a volume of 200 to 300 µl. To the concentrate was added 25 µl of 8 M urea and 0.4 M $NH_4HCO_3$, and the mixture was concentrated to an extent giving a solution remained at a volume of 100 µl or lower. The concentrate was brought to about 100 µl with purified water, and the mixture was filtered through a filter of Ultrafree™ C3 GV (Millipore). The filtrate obtained was then subjected to elution through a column of Aquapore™ BU-300 C-4 (2.1 mm×300 mm) by a gradient of 0.1% TFA/2.1% to 68.6% acetonitrile. Absorbance at 215 nm was monitored to collect a fraction at a peak thereof. The sample collected was evaporated under reduced pressure to complete dryness, and then analyzed with a Protein Sequencer 473A of ABI to determine a partial amino acid sequence of a raffinose synthase.

Example 5

Preparation of cDNA

About 2 g of immature seeds of broad bean (Nintoku Issun) was frozen in liquid nitrogen and then ground with a mortar, to which 20 ml of Isogen (Nippon Gene) was added, and the mixture was further thoroughly ground. The ground material was transferred into a centrifugation tube, to which 4 ml of chloroform was added, and the mixture was stirred with a vortex mixer and then centrifuged at 6,500×g for 10 minutes at 4° C. The water layer was collected, to which 10 ml of isopropanol was added, and the mixture was stirred and then centrifuged at 6,500×g for 10 minutes at 4° C. The resulting precipitate was washed with 10 ml of 70% ethanol and then dissolved in 1 ml of elution buffer (10 mM Tris-HCl (pH 7.5), 1 mM EDTA, 0.1% SDS). The solution was left at 60° C. for 10 minutes and then centrifuged at 10,000×g for 1 minute to remove insoluble matter. To the resulting supernatant was added an equivalent volume of Oligotex-dT30 (Takara), and the mixture was stirred and then left at 65° C. for 5 minutes. The mixture was placed on ice and then left for 3 minutes, to which 200 µl of 5 M NaCl was added, and the mixture was left at 37° C. for 10 minutes. The mixture was then centrifuged at 10,000×g at 4° C. for 3 minutes. The precipitate was collected and then suspended in 1 ml of TE buffer, and the suspension was left at 65° C. for 5 minutes, which was placed on ice and then left for 3 minutes, followed by centrifugation at 10,000×g for 3 minutes at 4° C. to remove the precipitate.

To the resulting supernatant were added 100 µl of 3 M sodium acetate and 2 ml of ethanol, and RNA was ethanol precipitated and collected. The collected RNA was washed twice with 70% ethanol and then dissolved in 20 µl of sterilized water, which was used for the subsequent cDNA synthe- Amp PCR Systems 2400 and DNA Thermal Cycler Model 480 of Perkin-Elmer using Advantage KlenTaq cDNA Kit of Clontech. The polymerase chain reaction was effected with the above primers at 94° C. for 1 minute, at 50° C. for 3 minutes, and at 72° C. for 3 minutes, and this reaction was repeated forty times. As a result, the combinations of primers 8.2 (SEQ ID NO:48) and 13.3RV (SEQ ID NO:51), primers 13.4 (SEQ ID NO:49) and 10.3RV (SEQ ID NO:52), and primers 7.4 (SEQ ID NO:50) and 10.3RV (SEQ ID NO:52), having the nucleotide sequences shown in list 5 below, gave an amplification of 1.2 kb, 0.5 kb, and 1.2 kb bands, respectively. These amplified DNA fragments were cloned with a TA cloning kit (Invitrogen), followed by sequence reaction using ABI PRISM Dye Terminator Cycle Sequencing Ready Reaction Kit of Perkin-Elmer and nucleotide sequence analysis with a 373S DNA sequencer of ABI. As a result, these DNA fragments were found to have a nucleotide sequence extending from base 813 to base 1915, base 1936 to base 2413, and base 1226 to base 2413, respectively, in the nucleotide sequence of SEQ ID NO:1. Based on these nucleotide sequences, synthetic DNA primers having nucleotide sequences shown in list 6 below were prepared, and the nucleotide sequences in both terminal regions of cDNA were analyzed with Marathon cDNA Amplification Kit of Clontech. As a result, the nucleotide sequence of SEQ ID NO:1 was finally determined.

(List 5)

```
     #8.2   26mer
            AA(AG) AC(ATGC) GC(ATGC) CC(ATGC) AG(TC) AT(TCA) AT(TCA) GAC AA (SEQ ID NO:48)
    #13.4   20mer
            AA(AG) AT(TCA) TGG AA(TC) GT(ATGC) AAC AA (SEQ ID NO:49)
     #7.4   24mer
            AA(AG) GC(ATGC) AG(AG) GT(ATGC) GT(ATGC) GT(ATGC) CC(ATGC) AAG (SEQ ID NO:50)
  #13.3RV   21mer
            (TC)TT (AG)TT (ATGC)AG (AG)TT CCA (AGT)AT TTT (SEQ ID NO:51)
  #10.3RV   21mer
            (TC)TT (AG)TC (TC)TC (AG)TA (ATGC)AG (AG)AA TTT (SEQ ID NO:52)
```

(List 6)

```
   RS-2RV   30mer
            GGCTGAGGTTCGGTTCATTCCTGAATCATC (SEQ ID NO:53)
     RS-7   30mer
            CCAAATGGTACATATTGGCTCCAAGGTTGT (SEQ ID NO:54)
     RS-8   30mer
            AAGAGTGTATCTGAATTTTCACGCGCGGTG (SEQ ID NO:55)
     RS-9   30mer
            TGGTGCAATGGGAAAACTCCAATGAGCACC (SEQ ID NO:56)
    RS-10   30mer
            ATGAAGTGTTCTGATAGATTGAAAGTTTCG (SEQ ID NO:57)
    RS-11   30mer
            CAGTCTCTGGAGTTTGATGATAATGCAAGT (SEQ ID NO:58)
``` sis. The amount of RNA obtained was determined by the measurement of absorbance at 260 nm.

For the cDNA synthesis, First Strand Synthesis Kit for RT-PCR (Amercham) and cDNA Synthesis Kit (Takara) were used, and all operations were made according to the protocol.

Example 6

Nucleotide Sequence Analysis of Raffinose Synthase Gene from cDNA

Based on the amino acid sequence obtained in Example 4, mixed synthetic DNA primers having the nucleotide sequences (SEQ ID NOS:48-52) shown in list 5 below were synthesized. The PCR method was carried out with Gene Example 7

Cloning of Raffinose Synthase Gene from Broad Bean cDNA

The primers designed from the amino acid sequence of SEQ ID NO:2, i.e., primers having nucleotide sequences (SEQ ID NOS:59-60) shown in list 7 below, were synthesized. Using these primers and cDNA obtained in Example 5 as a template, a DNA fragment of the open reading frame region was amplified by PCR under the conditions described in Example 6. The amplified DNA fragment was digested with the restriction endonucleases Bam HI and Xba I whose recognition sequences were contained in the primers used. Using Ligation Kit (Takara), the DNA fragment thus digested was cloned in the plasmid pBluescriptII KS- (Stratagene) previously digested with Bam HI and Xba I. The nucleotide sequence of the cloned DNA fragment was confirmed with ABI PRISM Dye Terminator Cycle Sequencing Ready Reaction Kit of Perkin-Elmer. In the clone thus obtained, it was found that the base at position 1591 in the nucleotide sequence of SEQ ID NO:1 had been changed from thymine (T) to cytosine (C). This was, however, a nonsense mutation without a change of the amino acid; therefore, this clone was designated pBluescriptKS-RS™, and used in the subsequent experiment.

TABLE 1

| Transformant | Amount of raffinose produced (pmol) |
| --- | --- |
| HB101 (pGEX4T-3) | 0.56 |
| HB101 (pGEX-RS) | 10.50 |
| HB101 (pTrc-RS | 11.10 |

(List 7)

RS-N 41mer
    CGCGGATCCACCATGGCACCACCAAGCATAACCAAAACTGC (SEQ ID NO:59)

RS-C 37mer
    TGCTCTAGATTATCAAAATAAAAACTGGACCAAAGAC (SEQ ID NO:60)

Example 8

Expression of Broad Bean Raffinose Synthase Gene in *E. coli*

The plasmid pBluescriptKS-RS™ having the broad bean raffinose synthase gene obtained in Example 7 was digested with Bam HI and Not I, and cloned in the plasmid pGEX4T3 (Pharmacia) digested with Bam HI and Not I to give the plasmid pGEX-RS as shown in FIG. 1.

The plasmid pBluescriptKS-RS™ was digested with Nco I and Xba I, and cloned in the plasmid pTrc99A (Pharmacia) digested with Nco I and Xba I to give the plasmid pTrc-RS as shown in FIG. 1.

These plasmids were introduced into *E. coli* strain HB101, and the resulting transformants were used for the confirmation of raffinose synthase expression. Overnight cultures of the transformants were inoculated at a volume of 1 ml each into 100 ml of LB medium and incubated at 37° C. for about 3 hours, followed by the addition of IPTG (isopropylthio-β-D-galactoside) to a final concentration of 1 mM and further incubation for 5 hours. The cultures were centrifuged at 21,400×g for 10 minutes, and the bacterial cells were collected. The collected bacterial cells were stored at −80° C. To the frozen bacterial cells was added a 10-fold volume of 100 mM Tris-HCl (pH 7.4), 1 mM EDTA, 5 mM DTT (dithiothreitol), 1 mM PMSF (phenylmethylsulfonyl fluoride) and 1 mM benzamide, and the bacterial cells were thawed and suspended. These suspensions were treated with an ultrasonic disrupter (Branson) to effect the disruption of the bacterial cells. The disrupted cell mixtures obtained were centrifuged at 16,000×g for 10 minutes, and soluble protein solutions were collected.

The protein solutions thus obtained were used at a volume of 4 μl each for the measurement of raffinose synthase activity according to the method described above. The reaction was effected at 37° C. for 64 hours. As a control, *E. coli* strain HB101 that had been transformed with one of the vectors, pGEX-4T3, was used. The results are shown in Table 1. The synthesis of raffinose was detected in the samples from the transformants HB101 (pGEX-RS) and HB101 (pTrc-RS).

Example 9

Cloning of Raffinose Synthase Gene from Soybean cDNA

In the same manner as described in Example 5, cDNA was obtained from immature seeds of soybean (*Glycine Max*) Williams 82. Using this cDNA as a template and primers designed from the amino acid sequence of SEQ ID NO:2, i.e., primers having nucleotide sequences (SEQ ID NOS:61-64) shown in list 8 below, a DNA fragment was amplified by PCR under the conditions described in Example 6. The DNA fragment thus amplified by PCR was cloned with a TA cloning kit (Invitrogen), followed by sequence reaction using ABI PRISM Dye Terminator Cycle Sequencing Ready Reaction Kit of Perkin-Elmer and nucleotide sequence analysis with a 373S DNA sequencer of ABI. Based on this sequence, primers having nucleotide sequences (SEQ ID NOS:65-70) shown in list 9 below were synthesized. The synthesis of cDNA was carried out with Marathon Kit of Clontech using mRNA obtained in the same manner as described in Example 5 from leaves of soybean Williams 82. The cDNA obtained was ligated to an adaptor contained in this kit with ligase. This operation was made according to the protocol attached. Using the adaptor-ligated cDNA thus prepared, polymerase chain reaction was effected with the primers (SEQ ID NOS:65-70), shown in list 9 below. The nucleotide sequences in both terminal regions of the gene were analyzed according to the protocol attached to the Marathon Kit of Clontech. As a result, the nucleotide sequence of SEQ ID NO:3 was determined.

(List 8)

1-F primer 35mer
    CGATTIAAIGTITGGTGGACIACICAITGGGTIGG (SEQ ID NO:61)
2-RV primer 45mer
    GGCCTAIAAIGCITCCCAIGTICACCAICCIAAITTITCIATIAT (SEQ ID NO:62)

```
5-F primer  41mer
            CGATGGATGGCIAAITFITIATICAICCIGAITGGGAIATGTT (SEQ ID NO:63)
6-RV primer 32mer
            GGCCACATITTIACIA(AG)ICCIATIGGIGCIAA (SEQ ID NO:64
```

(List 9)

```
SN-1        30mer
            CACGAACTGGGGCACGAGACACAGATGATG (SEQ ID NO:65)
SC-3RV      30mer
            AAGCAAGTCACGGAGTGTGAATAGTCAGAG (SEQ ID NO:66)
SC-5        30mer
            ACACGAGACTGTTTGTTTGAAGACCCCTTG (SEQ ID NO:67)
SC-6        25mer
            TGGAATCTCAACAAATATACAGGTG (SEQ ID NO:68)
SN-3RV      30mer
            GGGTCATGGCCAACGTGGACGTATAAGCAC (SEQ ID NO:69)
SN-4RV      30mer
            GATGATCACTGGCGCGGTTTTCTCCTCGAG (SEQ ID NO:70)
```

Example 10

Acquisition of Raffinose Synthase Gene from Japanese Artichoke cDNA

In the same manner as described in Example 5, cDNA was obtained from leaves of Japanese artichoke (*Stachys sieboldii*). Using this cDNA as a template and primers designed from the amino acid sequence of SEQ ID NO:2, i.e., primers having nucleotide sequences (SEQ ID NOS:71-74) shown in list 10 below, a DNA fragment was amplified by PCR under the conditions described in Example 6. The DNA fragment thus amplified by PCR was cloned with a TA cloning kit (Invitrogen), followed by sequence reaction using ABI PRISM Dye Terminator Cycle Sequencing Ready Reaction Kit of Perkin-Elmer and nucleotide sequence analysis with a 373S DNA sequencer of ABI. As a result, the nucleotide sequence of SEQ ID:5 was determined.

Based on the nucleotide sequence thus obtained, synthesized DNA primers are prepared, and in the same manner as described in Example 9, the nucleotide sequences in both terminal regions of the gene are analyzed with Marathon Kit of Clontech.

Example 11

Acquisition of Raffinose Synthase Gene from Corn cDNA

In the same manner as described in Example 5, cDNA was obtained from leaves of corn (*Zea mays* L.) Pioneer 3358. Using this cDNA as a template and primers designed from the amino acid sequence of SEQ ID NO:2, i.e., primers having nucleotide sequences (SEQ ID NOS:75-76) shown in list 11 below, a DNA fragment was amplified by PCR under the conditions described in Example 6. The DNA fragment thus amplified by PCR was cloned with a TA cloning kit (Invitrogen), followed by sequence reaction using ABI PRISM Dye Terminator Cycle Sequencing Ready Reaction Kit of Perkin-Elmer and nucleotide sequence analysis with a 373S DNA sequencer of ABI. Based on this sequence, primers having nucleotide sequences (SEQ ID NOS:77-78) shown in list 12 below were synthesized. In the same manner as described in Example 5, mRNA obtained from leaves of corn (*Zea mays* L.) Pioneer 3358 was linked to an adaptor contained in the Marathon Kit of Clontech with ligase. This operation was made according to the protocol attached. Using the adaptor-ligated cDNA thus prepared, polymerase chain reaction was effected in the same manner as described above with the primers shown in list 12 (SEQ ID NOS:77-78) below. As a result, the nucleotide sequence of SEQ ID NO:7 was determined.

(List 10)

```
1-F primer  35mer
            CGATTIAAIGTITGGTGGACIACICAITGGGTIGG (SEQ ID NO:71)
4-RV primer 37mer
            GGCCAGCIATIACICCITTICCITTIAAITGITTITT (SEQ ID NO:72)
2-F primer  44mer
            CGAATIATIGAIAAITTIGGITGGTGIACITGGGAIGCITTITA (SEQ IDNO 73)
6-RV primer 32mer
            GGCCACATITTIACIA(AG)ICCIATIGGIGCIAA (SEO ID NO:74)
```

Based on the nucleotide sequence thus obtained, synthesized DNA primers are prepared, and in the same manner as described in Example 9, the nucleotide sequence in the 5'-terminal region of the gene is analyzed with Marathon Kit of Clontech.

pBI221(–). This pBI221(–) was used to prepare pBI221(–)-RS in the same manner as described for the preparation of pBI221-RS above.

Figure 2:
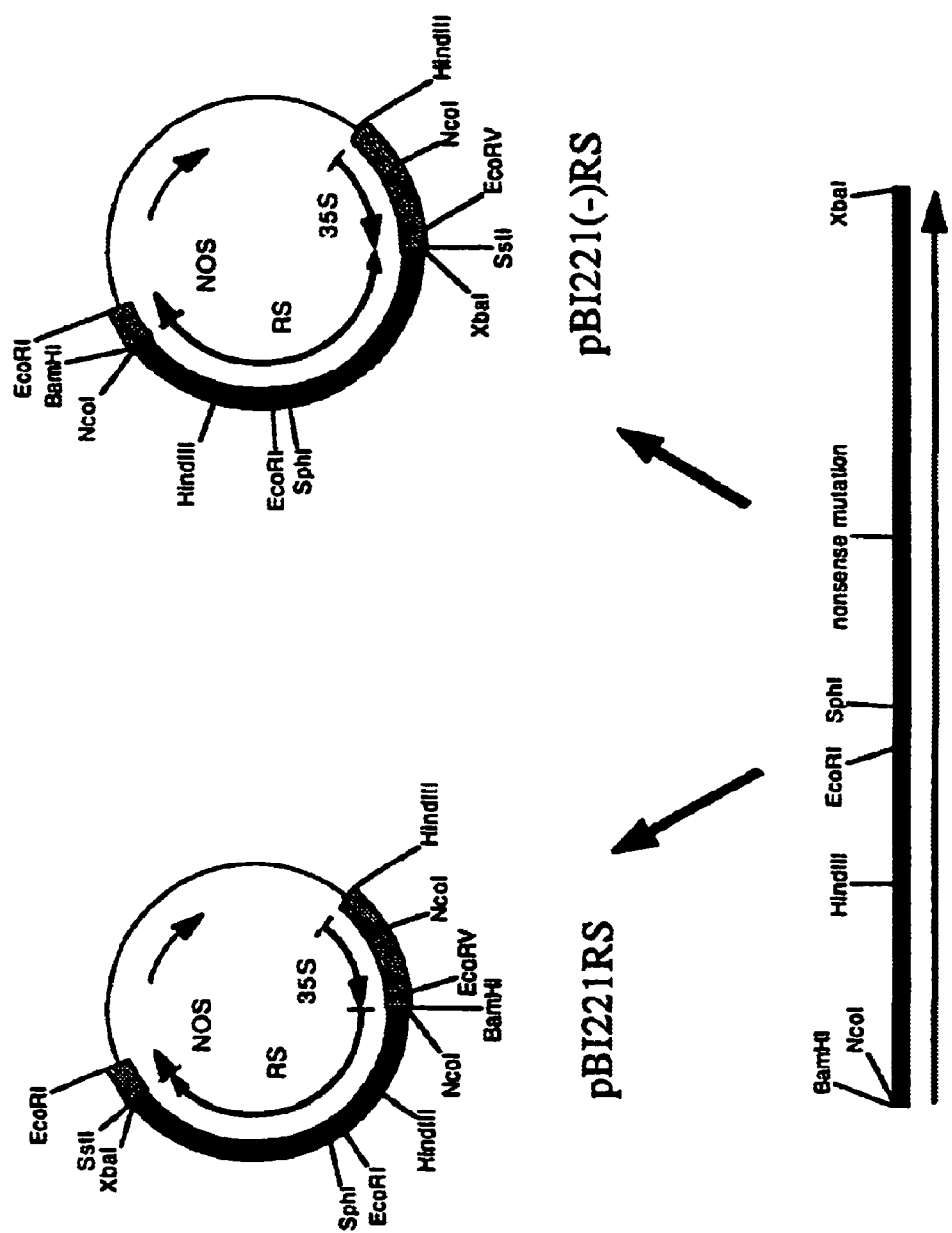
FIG. 2 shows the construction of expression vectors used for the expression in plants of chimera genes each having a raffinose synthase gene and a promoter linked thereto. The restriction endonuclease map of the raffinose synthase gene cloned in the plasmid pBluescriptKS-RS™ is shown in the lower portion of this figure. pBI221RS and pBI221(–)RS indicate the restriction endonuclease maps of expression vectors used for the transformation of soybean. 35S and NOS represent 35S promoter derived from cauliflower mosaic virus and nopaline synthase gene terminator, respectively.
Figure 3:
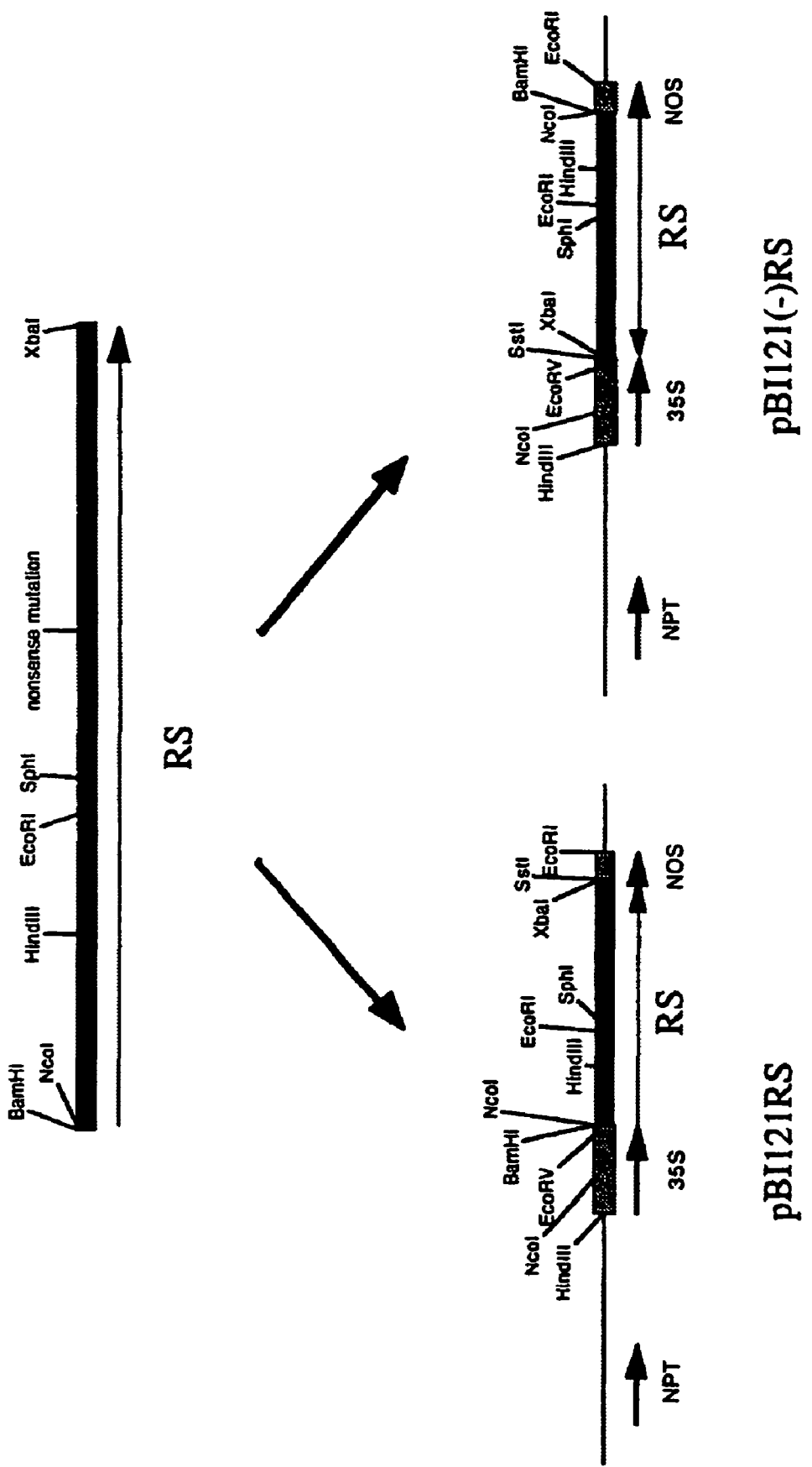
FIG. 3 shows the construction of expression vectors used for the expression in plants of chimera genes each having a raffinose synthase gene and a promoter linked thereto. The restriction endonuclease map of the raffinose synthase gene cloned in the plasmid pBluescriptKS-RS™ is shown in the upper portion of this figure. pBI121RS and pBI121(–)RS indicate the restriction endonuclease maps of binary vectors used for the transformation of mustard. For the binary vector, only a region between the right border and the left border is shown. 35S, NOS and NPT represent 35S promoter derived from cauliflower mosaic virus, nopaline synthase gene terminator and kanamycin resistance gene, respectively.

The construction of these expression vectors is shown in FIGS. 2 and 3.

(List 11)

```
5-F primer 41mer
       CGATGGATGGGIAAITTIATICAICCIGAITGGGAIATGTT  (SEQ ID NO:75)
6-RV primer 32mer
       GGCCACATITTIACIA(AG)ICCIATIGGIGCIAA  (SEQ ID NO:76)
```

(List 12)

```
M-10 primer 25mer
       GACGTCGAGTGGAAGAGCGGCAAGG  (SEQ ID NO:77)
M-11 primer 25mer
       CACCTACGAGCTCTTCGTCGTTGCC  (SEQ ID NO:78)
```

Example 12

Construction of Expression Vectors in Plant for Chimera Gene, 35S-Broad Bean Raffinose Synthase Gene The plasmid pBluescriptKS-RS™ having the broad bean raffinose synthase gene obtained in Example 7 was digested with the restriction endonucleases Bam HI and Sac I. Using Ligation Kit (Takara), the DNA fragment thus digested was cloned in the binary vector pBI121 (Clontech) previously digested with Bam HI and Sac I. The vector thus obtained was designated pBI121-RS.

For an antisense experiment, plasmid pBI121 (Clontech) previously digested with Bam HI and Sac I was ligated to linkers (SEQ ID NOS:79-80) shown in list 13 below to give pBI121(–). This pBI121(–) was used to prepare pBI121(–)-RS in the same manner as described for the preparation of pBI121-RS above.

A similar vector was prepared with pBI221. The plasmid pBluescriptKS-RS™ obtained in Example 7 was digested with the restriction endonucleases Bam HI and Sac I. Using Ligation Kit (Takara), the DNA fragment thus digested was cloned in the vector pBI221 (Clontech) previously digested with Bam HI and Sac I. The vector thus obtained was designated pBI221-RS.

For an antisense experiment, plasmid pBI221 (Clontech) previously digested with Bam HI and Sac I was ligated to linkers (SEQ ID NOS:79-80) shown in list 13 below to give (List 13)

```
BamSac-   25mer
  (+)     GATCGAGCTCGTGTCGGATCCAGCT  (SEQ ID NO:79)
  linker
BamSac-   17mer
  (–)     GGATCCGACACGAGCTC  (SEQ ID NO:80)
  linker
```

Example 13

Transformation of Mustard with Broad Bean Raffinose Synthase Gene

The vectors pBI121-RS and pBI121(–)-RS prepared in Example 12 were used for the transformation of mustard (*Brassica juncia*) by the *Agrobacterium* infection method.

*Agrobacterium tumefaciens* (strain C58C1, rifampicin resistant) previously made into a competent state by calcium chloride treatment was transformed independently with two plasmids pBI121-RS and pBI121(–)-RS prepared in Example 12. Selection for transformants was carried out on LB medium containing 50 µg/ml rifampicin and 25 µg/ml kanamycin by utilizing the character of kanamycin resistance conferred by the kanamycin resistance gene (neomycin phosphotransferase, NPTII) of the introduced plasmids.

The transformant *Agrobacterium* obtained (*Agrobacterium tumefaciens* strain C58, rifampicin resistant) was cultivated on LB medium containing 50 µg/ml rifampicin and 25 µg/ml kanamycin at 28° C. for a whole day and night, and the culture was used for the transformation of mustard by the method described below.

The seeds of mustard were aseptically sowed on ½ MS medium, 2% sucrose, 0.7% agar. After one week, cotyledons and petioles of sprouting plants were cut out with a scalpel, and transferred to MS medium, 3% sucrose, 0.7% agar, 4.5 µM BA, 0.05 µM 2.4-D, 3.3 µM AgNO$_3$, followed by precultivation for 1 day. The precultivated cotyledons and petioles were transferred in a 1000-fold dilution of the *Agrobacterium* culture to cause infection for 5 minutes. The infected cotyledons and petioles were transferred again to the same medium as used in the precultivation, and cultivated for 3 to 4 days. The cultivated cotyledons and petioles were transferred to MS medium, 3% sucrose, 4.5 µM BA, 0.05 µM 2.4-D, 3.3 µM AgNO$_3$, 500 mg/l cefotaxim, and sterilized with shaking for 1 day. The sterilized cotyledons and petioles were transferred to MS medium, 3% sucrose, 0.7% agar, 4.5 µM BA, 0.05 µM 2.4-D, 3.3 µM AgNO$_3$, 100 mg/l cefotaxim, 20 mg/l kanamycin, and cultivated for 3 to 4 weeks. The cotyledons and petioles were transferred to MS medium, 3% sucrose, 0.7% agar, 4.5 µM BA, 0.05 µM 2.4-D, 100 mg/l cefotaxim, 20 mg/l kanamycin, and cultivated. The cultivation on this medium was continued with subculturing at intervals of 3 to 4 weeks. When the regeneration of shoots began to occur, these shoots were subcultured on MS medium, 3% sucrose, 0.7% agar, 20 mg/l kanamycin, and cultivated for 3 to 4 weeks. The rooting plants were transferred to vermiculite:peat moss=1:1, and conditioned at 21° to 22° in a cycle of day/night=12 hours:12 hours. With the progress of plant body growth, the plants were suitably grown with cultivation soil. From leaves of the regenerated plants, genomic DNA was extracted according to the method described above, and the gene insertion into the plant genome was confirmed by PCR using the primers (SEQ ID NOS:81-84) shown in list 14 below.

```
              (List 14)

35S 30mer                              (SEQ ID NO:81)
         TTCCAGTATGGACGATTCAAGGCTTGCTTC
NOS 25mer                              (SEQ ID NO:82)
         ATGTATAATTGCGGGACTCTAATCA
RS-F 30mer                             (SEQ ID NO:83)
         AAGAGTGTATCTGAATTTTCACGCGCGGTG
RS-RV 33mer                            (SEQ ID NO:84)
         ACCTTCCCATACACCTTTTGGATGAACCTTCAA
```

Example 14

Transformation of Soybean Somatic Embryo with Broad Bean Raffinose Synthase Gene Cultured cells of soybean "Fayette" somatic embryos (400 to 500 mg FW) were arranged in one layer within a circle having a diameter of 20 mm on the central part of a 6 cm agar plate. Two plasmids pBI221-RS and pBI221 (–)-RS having chimera genes prepared from the broad bean raffinose synthase gene and 35S promoter in Example 12 were introduced into the soybean somatic embryos according to the disclosure of the Japanese Patent Application No. 3-291501/1991. That is, these plasmids were mixed with the β-glucuronidase (GUS)/hygromycin-resistant gene (HPT) coexpression vector pSUM-GH:NotI for selection described in Soshiki Baiyo, 20, 323-327 (1994). These mixed plasmids were used for the gene introduction into the soybean somatic embryos with a particle gun (800 mg/coating gold particles 200 µg/shot; projectile stopper-sample distance, 100 mm). After the introduction, gyratory cultures were grown in the MS modified growth liquid medium (Sigma) containing 25 to 50 µg/ml hygromycin under illumination at 25° C. for 16 hours, and transformed somatic embryos were selected.

For the hygromycin-resistant soybean somatic embryos having yellowish green color and growth ability, which were selected after about 3 months, polymerization chain reaction is effected with primers (SEQ ID NOS:81-84) shown in list 14 above to determine whether the broad bean raffinose synthase gene region is amplified or not. This confirms that the broad bean raffinose synthase gene is inserted into the soybean genome.

Furthermore, the somatic embryos obtained are used for the regeneration of plants to give transformant soybean with the broad bean raffinose synthase gene.

Medium Composition

LB and MS media used in the above Examples have the following respective compositions.

| (LB medium) | |
|---|---|
| Bacto-tryptone | 10 g |
| Bacto-yeast extract | 5 g |
| NaCl | 10 g/1 liter H2O (pH 7.0) |
| (MS medium) | |
| KNO3 | 2022 mg/l |
| NH4NO3 | 1650 mg/l |
| NH4Cl | 2140 mg/l |
| KH2PO4 | 170 mg/l |
| MgSO4•7H2O | 370 mg/l |
| CaCl2•2H2O | 440 mg/l |
| MnSO4•4H2O | 22.3 mg/l |
| ZnSO4•7H2O | 8.6 mg/l |
| CuSO4•5H2O | 0.025 mg/l |
| KI | 0.83 mg/l |
| CoCl2•6H2O | 0.025 mg/l |
| H3BO3 | 6.2 mg/l |
| NaMoO4•2H2O | 0.25 mg/l |
| FeSO4•7H2O | 27.8 mg/l |
| Na2EDTA | 37.3 mg/l |
| Nicotinic acid | 0.5 mg/l |
| Thiamine HCl | 1 mg/l |
| Pyridoxine HCl | 0.5 mg/l |
| Inositol | 100 mg/l |
| Glycine | 2 mg/l |

Brief Description of the Sequences

1. SEQ ID NO:2:

The sequence of SEQ ID NO:2 shows an amino acid sequence of a raffinose synthase protein encoded in the raffinose synthase gene obtained from broad bean.

2. SEQ ID NO:1:

The sequence of SEQ ID NO:1 shows a cDNA nucleotide sequence of the raffinose synthase gene obtained from broad bean.

3. SEQ ID NO:4 shows NO:4:

The sequence of SEQ ID NO:4 shows an amino acid sequence of a raffinose synthase protein encoded in the raffinose synthase gene obtained from soybean.

4. SEQ ID NO:3:

The sequence of SEQ ID NO:3 shows a cDNA nucleotide sequence of the raffinose synthase gene obtained from soybean.

5. SEQ ID NO:6:

The sequence of SEQ ID NO:6 shows an amino acid sequence of a raffinose synthase protein encoded in the raffinose synthase gene obtained from Japanese artichoke.

6. SEQ ID NO:5:

The sequence of SEQ ID NO:5 shows a cDNA nucleotide sequence of the raffinose synthase gene obtained from Japanese artichoke.

7. SEQ ID NO:8:

The sequence of SEQ ID NO:8 shows an amino acid sequence of a raffinose synthase protein encoded in the raffinose synthase gene obtained from corn.

8. SEQ ID NO:7:

The sequence of SEQ ID NO:7 shows a cDNA nucleotide sequence of the raffinose synthase gene obtained from corn.

9. List 1:

The nucleotide sequences (SEQ ID NOS:9-14) shown in list 1 are of the typical primers used in the amplification of a cDNA fragment of a raffinose synthase gene. All of these sequences are based on the nucleotide sequence in the non-coding region of the gene. Primer 1 (SEQ ID NO:9) is a sense primer corresponding to the 5'-terminus of a cDNA fragment of the broad bean-derived raffinose synthase gene. Primers 2 (SEQ ID NO:10) and 3 2 (SEQ ID NO:11) are antisense primers corresponding to the 3'-terminus of the cDNA fragment of the broad bean-derived raffinose synthase gene. Primer 4 (SEQ ID NO:12) is a sense primer corresponding to the 5'-terminus of a cDNA fragment of the soybean-derived raffinose synthase gene. Primers 5 (SEQ ID NO:13) and 6 (SEQ ID NO:14) are antisense primers corresponding to the 3'-terminus of the cDNA fragment of the soybean-derived raffinose synthase gene. Depending upon the purpose, recognition sequences for suitable restriction endonucleases can be added to the 5'-termini of these nucleotide sequences in an appropriate manner.

10. List 2:

The nucleotide sequences (SEQ ID NOS:15-22) shown in list 2 are of the typical primers used in the amplification of an open reading frame coding for the amino acid sequence of a raffinose synthase protein in the cDNA sequence of a raffinose synthase gene. Primers 1 (SEQ ID NO:15) and 2 (SEQ ID NO:16) are sense primers corresponding to the N-terminus of the broad bean-derived raffinose synthase protein. Primers 3 (SEQ ID NO:17) and 4 (SEQ ID NO:18) are antisense primers corresponding to the C-terminus of the broad bean-derived raffinose synthase protein. Primers 5 (SEQ ID NO:19) and 6 (SEQ ID NO:20) are sense primers corresponding to the N-terminus of the soybean-derived raffinose synthase protein. Primers 7 (SEQ ID NO:21) and 8 (SEQ ID NO:22) are antisense primers corresponding to the C-terminus of the soybean-derived raffinose synthase protein. Depending upon the purpose, recognition sequences for suitable restriction endonucleases can be added to the 5'-termini of these sequences in an appropriate manner.

11. List 3:

The amino acid sequences (SEQ ID NOS:23-37) shown in list 3 are partial amino acid sequences of a raffinose synthase protein.

1 (SEQ ID NO:23) is equivalent to the partial amino acid sequence extending from amino acid 110 to amino acid 129 in the amino acid sequence of SEQ ID NO:2.

2 (SEQ ID NO:24) is equivalent to the partial amino acid sequence extending from amino acid 234 to amino acid 247 in the amino acid sequence of SEQ ID NO:2.

3 (SEQ ID NO:25) is equivalent to the partial amino acid sequence extending from amino acid 265 to amino acid 279 in the amino acid sequence of SEQ ID NO:2.

4 (SEQ ID NO:26) is equivalent to the partial amino acid sequence extending from amino acid 296 to amino acid 312 in the amino acid sequence of SEQ ID NO:2.

5 (SEQ ID NO:27) is equivalent to the partial amino acid sequence extending from amino acid 346 to amino acid 361 in the amino acid sequence of SEQ ID NO:2.

6 (SEQ ID NO:28) is equivalent to the partial amino acid sequence extending from amino acid 383 to amino acid 402 in the amino acid sequence of SEQ ID NO:2.

7 (SEQ ID NO:29) is equivalent to the partial amino acid sequence extending from amino acid 411 to amino acid 433 in the amino acid sequence of SEQ ID NO:2.

8 (SEQ ID NO:30) is equivalent to the partial amino acid sequence extending from amino acid 440 to amino acid 453 in the amino acid sequence of SEQ ID NO:2.

9 (SEQ ID NO:31) is equivalent to the partial amino acid sequence extending from amino acid 457 to amino acid 468 in the amino acid sequence of SEQ ID NO:2.

10 (SEQ ID NO:32) is equivalent to the partial amino acid sequence extending from amino acid 471 to amino acid 516 in the amino acid sequence of SEQ ID NO:2.

11 (SEQ ID NO:33) is equivalent to the partial amino acid sequence extending from amino acid 517 to amino acid 559 in the amino acid sequence of SEQ ID NO:2.

12 (SEQ ID NO:34) is equivalent to the partial amino acid sequence extending from amino acid 574 to amino acid 582 in the amino acid sequence of SEQ ID NO:2.

13 (SEQ ID NO:35) is equivalent to the partial amino acid sequence extending from amino acid 586 to amino acid 609 in the amino acid sequence of SEQ ID NO:2.

14 (SEQ ID NO:36) is equivalent to the partial amino acid sequence extending from amino acid 615 to amino acid 627 in the amino acid sequence of SEQ ID NO:2.

15 (SEQ ID NO:37) is equivalent to the partial amino acid sequence extending from amino acid 716 to amino acid 724 in the amino acid sequence of SEQ ID NO:2.

12. List 4:

The nucleotide sequences (SEQ ID NOS:38-47) shown in list 4 are of the typical primers synthesized on some of the amino acid sequences (SEQ ID NOS:23-37) shown in list 3. The symbol "F" as used after the primer number means that the primer referred to by this symbol has a sense sequence. The symbol "RV" as used after the primer number means that the primer referred to by this symbol has an antisense sequence. Primer (1-F (SEQ ID NO:38)) corresponds to the nucleotide sequence which codes for the partial amino acid sequence extending from amino acid 119 to amino acid 129 in the amino acid sequence of SEQ ID NO:2. Primers 2-F (SEQ ID NO:39) and 2-RV (SEQ ID NO:40) correspond to the nucleotide sequences that code for the partial amino acid sequence extending from amino acid 234 to amino acid 247 in the amino acid sequence of SEQ ID NO:1. Primers 3-F (SEQ ID NO:41) and 3-RV (SEQ ID NO:42) correspond to the nucleotide sequences that code for the partial amino acid sequence extending from amino acid 265 to amino acid 279 in the amino acid sequence of SEQ ID NO:2. Primers 4-F (SEQ ID NO:43) and 4-RV (SEQ ID NO:44) correspond to the nucleotide sequences that code for the partial amino acid sequence extending from amino acid 458 to amino acid 468 in the amino acid sequence of SEQ ID NO:2. Primers 5-F (SEQ ID NO:45) and 5-RV (SEQ ID NO:46) correspond to the nucleotide sequences that code for partial amino acid sequence extending from amino acid 522 to amino acid 534 in the amino acid sequence of SEQ ID NO:2. Primers 6-RV (SEQ ID NO:47) correspond to the nucleotide sequences that code for the partial amino acid sequence extending from amino acid 716 to amino acid 724 in the amino acid sequence of SEQ ID NO:2.

13. List 5:

The nucleotide sequences (SEQ ID NOS:48-52) shown in list 5 are of the typical primers synthesized on the partial amino acid sequences of the purified broad bean raffinose synthase protein. The bases shown in parentheses mean that a mixture of those bases was used in the synthesis. The symbol "RV" as used after the primer number means that the primer referred to by this symbol has an antisense sequence.

14. List 6:

The nucleotide sequences (SEQ ID NOS:53-58) shown in list 6 are of the typical primers used in the analysis of both terminal regions of a cDNA nucleotide sequence of the broad bean raffinose synthase gene by the RACE method. The symbol "RV" as used after the primer number means that the primer referred to by this symbol has an antisense sequence.

15. List 7:

The nucleotide sequences (SEQ ID NOS:59-60) shown in list 7 are of the typical primers used in the cloning of the broad bean raffinose synthase gene. RS-N corresponds to the N-terminus of the open reading frame and contains two recognition sites for the restriction endonucleases Bam HI and Nco I on the 5'-terminal side. RS-C is an antisense primer corresponding to the C-terminus of the open reading frame and contains a recognition site for the restriction endonuclease Xba I on the 5'-terminal side.

16. List 8:

The nucleotide sequences SEQ ID NOS:61-64) shown in list 8 are of the typical primers used in the cloning of a soybean raffinose synthase gene fragment. The base represented by the symbol "I" was inosine used in the synthesis. The symbol "RV" as used after the primer number means that the primer referred to by this symbol has an antisense sequence.

17. List 9:

The nucleotide sequences (SEQ ID NOS:65-70) shown in list 9 are of the typical primers used in the analysis of the cDNA nucleotide sequence of a soybean raffinose synthase gene fragment. The symbol "RV" as used after the primer number means that the primer referred to by this symbol has an antisense sequence.

The analysis of nucleotide sequences was carried out by polymerase chain reaction using SN-1 and SC-3RV. SC-5 and SC-6 were used in the analysis of a nucleotide sequence in the 3'-terminal region, and SN-3RV and SN-4RV were used in the analysis of a nucleotide sequence in the 5'-terminal region.

18. List 10:

The nucleotide sequences (SEQ ID NOS:71-74) shown in list 10 are of the typical primers used in the analysis of the cDNA nucleotide sequence of a Japanese artichoke raffinose synthase gene fragment. The base represented by the symbol "I" was inosine used in the synthesis. The symbol "RV" as used after the primer number means that the primer referred to by this symbol has an antisense sequence.

19. List 11:

The nucleotide sequences (SEQ ID NOS:75-76) shown in list 11 are of the typical primers used in the analysis of the cDNA nucleotide sequence of a corn raffinose synthase gene fragment. The base represented by the symbol "I" was inosine used in the synthesis. The symbol "RV" as used after the primer number means that the primer referred to by this symbol has an antisense sequence.

20. List 12:

The nucleotide sequences (SEQ ID NOS:77-78) shown in list 12 are of the typical primers used in the analysis of the cDNA nucleotide sequence of a corn raffinose synthase gene fragment. M-10 and M-11 were used in the analysis of a nucleotide sequence in the 3'-terminal region.

21. List 13:

The nucleotide sequences (SEQ ID NOS:79-80) shown in list 13 are of the typical adopters used in the construction of vectors for antisense experiments. These synthetic DNA fragments takes a double-stranded form when mixed together because they are complementary strands. This double-stranded DNA fragment has cohesive ends of cleavage sites for the restriction endonucleases Bam HI and Sac I on both termini, and contains the restriction sites for the restriction endonucleases Bam HI and Sac I in the double-stranded region.

22. List 14:

The nucleotide sequences (SEQ ID NOS:81-84) shown in list 14 are of the typical primers used in the PCR experiment to confirm the gene introduction into the genome of a recombinant plant. 35S is a primer toward the downstream region at the 35S promoter site, and NOS is a primer toward the upstream region at the NOS terminator site. RS-F is a sense primer of the broad bean raffinose synthase gene, and RS-RV is an antisense primer of the broad bean raffinose synthase gene.

TABLE 1

| Code | Protein* | Organism | Accession** | Reference | Author/Assignee |
|---|---|---|---|---|---|
| Sc-03 | RFS | *Beta vulgaris* | E37133 | 09/301,766 | Sumitomo Chemical |
| Sc-05 | RFS | *Brassica juncea* | E36417 | 09/301,766 | Sumitomo Chemical |
| Sc-02 | RFS | *Vicia faba* | E24423 | 08/992,914 | Sumitomo Chemical |
| Sc-04 | RFS | *Glycine max* | E24424 | 08/992,914 | Sumitomo Chemical |
| Aj-05 | RFS | *Cucumis sativus* | AF073744 | Family GH36*** | Ohsumi et al. |
| PsRFS | RFS | *Pisum sativum* | AJ426475 | Family GH36 | Peterbauer et al. |
| HvSIP | SIP | *Hordeum vulgare* | M77475 | Family GH36 | Heck et al. |
| PsSTS-1 | STS | *Pisum sativum* | AJ311087 | Family GH36 | Peterbauer et al. |
| PsSTS-2 | STS | *Pisum sativum* | AJ512932 | Family GH36 | Peterbauer et al. |
| VaSTS | STS | *Vigna angularis* | Y19024 | Family GH36 | Peterbauer et al. |
| AmSTS | STS | *Alonsoa meridionalis* | AJ487030 | Family GH36 | Voitsekhovskaja |
| SsSTS | STS | *Stachys affinis* | AJ344091 | Family GH36 | Pesch and Schmitz |

*Protein: RFS, Raffinose synthase; SIP, Seed Imbibition Protein; STS, Stachyose synthase.
**Accession: GenBank Accession Number.
***Family GH36: glycoside hydrolase family 36 (see Carbohydrate-Active Enzymes (CAZy) database: http://afmb.cnrs-mrs.fr/CAZY/GH_36.html)

TABLE 2

| Code | Sc02 | Sc03 | Sc04 | Sc05 | PsRFS | Aj-05 | HvSIP | AmSTS | PaSTS-1 | PsSTS-2 | SaSTS | VaSTS |
|---|---|---|---|---|---|---|---|---|---|---|---|---|
| amino acids | 800 | 783 | 611 | 777 | 798 | 784 | 757 | 868 | 853 | 847 | 863 | 857 |
| Sc-02 | | 62 | 54 | 62 | 89 | 84 | 39 | 43 | 43 | 42 | 42 | 43 |
| Sc-03 | | | 50 | 63 | 63 | 66 | 39 | 42 | 43 | 42 | 42 | 43 |
| Sc-04 | . | | | 50 | 54 | 50 | 29 | 35 | 35 | 35 | 34 | 36 |
| Sc-05 | | | | | 62 | 70 | 39 | 44 | 44 | 43 | 44 | 45 |
| PsRFS | | | | | | 64 | 38 | 42 | 43 | 43 | 42 | 43 |

TABLE 2-continued

| Code | Sc02 | Sc03 | Sc04 | Sc05 | PsRFS | Aj-05 | HvSIP | AmSTS | PaSTS-1 | PsSTS-2 | SaSTS | VaSTS |
|---|---|---|---|---|---|---|---|---|---|---|---|---|
| Aj-05 | | | | | | | 38 | 42 | 44 | 43 | 43 | 43 |
| HvSIP | | | | | | | | 33 | 34 | 34 | 34 | 34 |
| AmSTS | | | | | | | | | 64 | 64 | 83 | 64 |
| PsSTS-1 | | | | | | | | | | 98 | 65 | 75 |
| PsSTS-2 | | | | | | | | | | | 65 | 74 |
| SaSTS | | | | | | | | | | | | 65 |
| VaSTS | | | | | | | | | | | | |

---

The invention claimed is:

1. An isolated nucleic acid comprising the nucleotide sequence of SEQ ID NO:1.

2. An isolated nucleic acid comprising a nucleotide sequence coding for the amino acid sequence of SEQ ID NO:2.

3. An isolated nucleic acid comprising a nucleotide sequence coding for an amino acid sequence of a protein which produces raffinose by combining a D-galactosyl group through an α(1→6) bond with a hydroxyl group attached to the carbon atom at position 6 of a D-glucose residue in a sucrose molecule, wherein said nucleotide sequence comprises a nucleotide sequence selected from the group consisting of:

(a) the nucleotide sequence of SEQ ID NO:1, and (b) a nucleotide sequence encoding the amino acid sequence of SEQ ID NO:2.

4. A chimeric gene comprising a nucleic acid comprising a nucleotide sequence coding for an amino acid sequence of a protein which produces raffinose by combining a D-galactosyl group through an α(1→6) bond with a hydroxyl group attached to the carbon atom at position 6 of a D-glucose residue in a sucrose molecule, wherein said nucleotide sequence comprises a nucleotide sequence selected from the group consisting of:
  (a) the nucleotide sequence of SEQ ID NO:1, and
  (b) a nucleotide sequence encoding the amino acid sequence of SEQ ID NO:2.

5. A plasmid comprising a nucleic acid comprising a nucleotide sequence coding for an amino acid sequence of a protein which produces raffinose by combining a D-galactosyl group through an α(1→6) bond with a hydroxyl group attached to the carbon atom at position 6 of a D-glucose residue in a sucrose molecule, wherein said nucleotide sequence comprises a nucleotide sequence selected from the group consisting of:
  (a) the nucleotide sequence of SEQ ID NO:1, and
  (b) a nucleotide sequence encoding the amino acid sequence of SEQ ID NO:2.

6. A method for metabolic modification, which comprises introducing a nucleic acid comprising a nucleotide sequence coding for an amino acid sequence of a protein which produces raffinose by combining a D-galactosyl group through an α(1→6) bond with a hydroxyl group attached to the carbon atom at position 6 of a D-glucose residue in a sucrose molecule, wherein said nucleotide sequence comprises a nucleotide sequence selected from the group consisting of:
  (a) the nucleotide sequence of SEQ ID NO:1, and
  a nucleotide sequence encoding the amino acid sequence of SEQ ID NO:2.

* * * * *

SEQUENCE LISTING

<160> NUMBER OF SEQ ID NOS: 87

<210> SEQ ID NO 1
<211> LENGTH: 2746
<212> TYPE: DNA
<213> ORGANISM: Vicia faba
<220> FEATURE:
<221> NAME/KEY: CDS
<222> LOCATION: (101)..(2497)

<400> SEQUENCE: 1

```
aattttcaag catagccaag ttaaccacct tagaaacatt cctacaagct acttatccct        60
gtcaataagc tactaagcta ccagagtctc atcaatcacc atg gca cca cca agc       115
                                            Met Ala Pro Pro Ser
                                             1               5 ata acc aaa act gca acc ctc caa gac gta ata agc acc atc gat att       163
Ile Thr Lys Thr Ala Thr Leu Gln Asp Val Ile Ser Thr Ile Asp Ile
            10                  15                  20 ggt aat ggt aac tca ccc tta ttc tcc ata acc tta gac caa tca cgt       211
Gly Asn Gly Asn Ser Pro Leu Phe Ser Ile Thr Leu Asp Gln Ser Arg
        25                  30                  35 gac ttc ctt gca aat ggc cac cct ttc ctc acc caa gtc cca cct aac       259
Asp Phe Leu Ala Asn Gly His Pro Phe Leu Thr Gln Val Pro Pro Asn
    40                  45                  50 ata aca aca aca aca aca acc act gct tcc tct ttt ctc aat ctc aaa       307
Ile Thr Thr Thr Thr Thr Thr Thr Ala Ser Ser Phe Leu Asn Leu Lys
55                  60                  65 tcc aac aaa gat acc att ccc aac aac aac aac acc atg ttg ttg caa       355
Ser Asn Lys Asp Thr Ile Pro Asn Asn Asn Asn Thr Met Leu Leu Gln
 70                  75                  80                  85 caa ggt tgt ttc gtt ggt ttc aac tcc acc gaa ccc aaa agc cac cac       403
Gln Gly Cys Phe Val Gly Phe Asn Ser Thr Glu Pro Lys Ser His His
                90                  95                 100 gta gtt cca ctc ggc aaa cta aaa gga atc aaa ttc atg agc ata ttc       451
Val Val Pro Leu Gly Lys Leu Lys Gly Ile Lys Phe Met Ser Ile Phe
            105                 110                 115 cgg ttc aaa gtt tgg tgg aca act cac tgg gtc gga aca aat gga cag       499
Arg Phe Lys Val Trp Trp Thr Thr His Trp Val Gly Thr Asn Gly Gln
        120                 125                 130 gaa cta caa cac gaa aca caa atg tta atc ctg gac aaa aac gac tcc       547
Glu Leu Gln His Glu Thr Gln Met Leu Ile Leu Asp Lys Asn Asp Ser
    135                 140                 145 ctc gga cga ccc tat gtc tta ctc ctc cca atc cta gaa aac acc ttc       595
Leu Gly Arg Pro Tyr Val Leu Leu Leu Pro Ile Leu Glu Asn Thr Phe
150                 155                 160                 165 cga acc tca ctc caa ccc ggt ctc aac gat cac ata ggc atg tcc gtc       643
Arg Thr Ser Leu Gln Pro Gly Leu Asn Asp His Ile Gly Met Ser Val
                170                 175                 180
```

```
gaa agc ggt tca aca cat gtc acc ggg tca agc ttc aaa gca tgt ctt    691
Glu Ser Gly Ser Thr His Val Thr Gly Ser Ser Phe Lys Ala Cys Leu
            185                 190                 195 tac atc cat ctc agt aac gac cca tac agt ata cta aaa gaa gca gtt    739
Tyr Ile His Leu Ser Asn Asp Pro Tyr Ser Ile Leu Lys Glu Ala Val
        200                 205                 210 aaa gta atc caa act cag tta gga aca ttc aag act ctt gaa gaa aaa    787
Lys Val Ile Gln Thr Gln Leu Gly Thr Phe Lys Thr Leu Glu Glu Lys
    215                 220                 225 aca gca cct agt att ata gac aaa ttc ggt tgg tgc acg tgg gat gct    835
Thr Ala Pro Ser Ile Ile Asp Lys Phe Gly Trp Cys Thr Trp Asp Ala
230                 235                 240                 245 ttt tac ttg aag gtt cat cca aaa ggt gta tgg gaa ggt gta aag tct    883
Phe Tyr Leu Lys Val His Pro Lys Gly Val Trp Glu Gly Val Lys Ser
                250                 255                 260 ctc aca gat ggt ggt tgt cct ccc ggt ttc gtc ata atc gac gac ggt    931
Leu Thr Asp Gly Gly Cys Pro Pro Gly Phe Val Ile Ile Asp Asp Gly
            265                 270                 275 tgg caa tcc att tgt cat gac gat gac gat gaa gat gat tca gga atg    979
Trp Gln Ser Ile Cys His Asp Asp Asp Asp Glu Asp Asp Ser Gly Met
        280                 285                 290 aac cga acc tca gcc ggg gaa caa atg cca tgc aga ctt gta aaa tac   1027
Asn Arg Thr Ser Ala Gly Glu Gln Met Pro Cys Arg Leu Val Lys Tyr
    295                 300                 305 gaa gag aat tct aag ttt aga gaa tat gag aat cct gaa aat gga ggg   1075
Glu Glu Asn Ser Lys Phe Arg Glu Tyr Glu Asn Pro Glu Asn Gly Gly
310                 315                 320                 325 aag aaa ggt ttg ggt ggt ttt gtg agg gat ttg aag gaa gag ttt ggg   1123
Lys Lys Gly Leu Gly Gly Phe Val Arg Asp Leu Lys Glu Glu Phe Gly
                330                 335                 340 agt gtg gag agt gtt tat gtt tgg cat gcg ctt tgt ggg tat tgg ggc   1171
Ser Val Glu Ser Val Tyr Val Trp His Ala Leu Cys Gly Tyr Trp Gly
            345                 350                 355 ggg gtt agg cct gga gtg cat ggg atg ccg aaa gct agg gtt gtt gtt   1219
Gly Val Arg Pro Gly Val His Gly Met Pro Lys Ala Arg Val Val Val
        360                 365                 370 ccg aag gtg tct cag ggg ttg aag atg acg atg gag gat ttg gcg gtg   1267
Pro Lys Val Ser Gln Gly Leu Lys Met Thr Met Glu Asp Leu Ala Val
    375                 380                 385 gat aag att gtt gag aac ggt gtg ggg cta gtg ccg cca gat ttt gca   1315
Asp Lys Ile Val Glu Asn Gly Val Gly Leu Val Pro Pro Asp Phe Ala
390                 395                 400                 405 cat gag atg ttt gat ggg ctt cac tct cat ttg gag tcg gcg gga att   1363
His Glu Met Phe Asp Gly Leu His Ser His Leu Glu Ser Ala Gly Ile
                410                 415                 420 gac ggt gtt aaa gtt gat gtt atc cat ctg ctt gag tta cta tca gag   1411
Asp Gly Val Lys Val Asp Val Ile His Leu Leu Glu Leu Leu Ser Glu
            425                 430                 435 gaa tat ggt gga cga gtt gag cta gca aga gct tat tac aaa gca cta   1459
Glu Tyr Gly Gly Arg Val Glu Leu Ala Arg Ala Tyr Tyr Lys Ala Leu
        440                 445                 450 acc tca tca gtg aag aaa cat ttc aaa ggc aat ggt gta att gct agc   1507
Thr Ser Ser Val Lys Lys His Phe Lys Gly Asn Gly Val Ile Ala Ser
    455                 460                 465 atg gag cat tgc aac gac ttc ttt ctc ctc ggc acc gaa gcc ata tcc   1555
Met Glu His Cys Asn Asp Phe Phe Leu Leu Gly Thr Glu Ala Ile Ser
470                 475                 480                 485 ctc ggc cgc gtc gga gat gat ttt tgg tgc tct gat cca tct ggt gat   1603
Leu Gly Arg Val Gly Asp Asp Phe Trp Cys Ser Asp Pro Ser Gly Asp
```

-continued

| | | 490 | | | | 495 | | | | 500 | | | | |
|---|---|---|---|---|---|---|---|---|---|---|---|---|---|---|
| cca | aat | ggt | aca | tat | tgg | ctc | caa | ggt | tgt | cac | atg | gta | cat | tgt | gcc | 1651 |
| Pro | Asn | Gly | Thr | Tyr | Trp | Leu | Gln | Gly | Cys | His | Met | Val | His | Cys | Ala |
| | | 505 | | | | | 510 | | | | | 515 | | | |

| tac | aac | agt | tta | tgg | atg | gga | aat | ttc | att | cag | cca | gat | tgg | gac | atg | 1699 |
| Tyr | Asn | Ser | Leu | Trp | Met | Gly | Asn | Phe | Ile | Gln | Pro | Asp | Trp | Asp | Met |
| | | 520 | | | | | 525 | | | | | 530 | | | |

| ttt | cag | tcc | act | cat | cct | tgt | gct | gaa | ttt | cat | gcc | gcc | tca | cga | gcc | 1747 |
| Phe | Gln | Ser | Thr | His | Pro | Cys | Ala | Glu | Phe | His | Ala | Ala | Ser | Arg | Ala |
| | 535 | | | | | 540 | | | | | 545 | | | | |

| ata | tcc | ggc | gga | cca | att | tat | gtt | agt | gat | tgt | gtt | ggt | aat | cac | aat | 1795 |
| Ile | Ser | Gly | Gly | Pro | Ile | Tyr | Val | Ser | Asp | Cys | Val | Gly | Asn | His | Asn |
| 550 | | | | | 555 | | | | | 560 | | | | | 565 |

| ttc | aag | ttg | ctc | aaa | tct | ctt | gtt | ttg | ccc | gat | ggt | tct | atc | ttg | cgt | 1843 |
| Phe | Lys | Leu | Leu | Lys | Ser | Leu | Val | Leu | Pro | Asp | Gly | Ser | Ile | Leu | Arg |
| | | | | 570 | | | | | 575 | | | | | 580 | |

| tgt | caa | cat | tac | gca | ctc | cct | aca | aga | gat | tgc | ttg | ttt | gaa | gac | cct | 1891 |
| Cys | Gln | His | Tyr | Ala | Leu | Pro | Thr | Arg | Asp | Cys | Leu | Phe | Glu | Asp | Pro |
| | | | 585 | | | | | 590 | | | | | 595 | | |

| ttg | cat | aat | ggc | aaa | aca | atg | ctg | aaa | att | tgg | aat | ctc | aac | aaa | tat | 1939 |
| Leu | His | Asn | Gly | Lys | Thr | Met | Leu | Lys | Ile | Trp | Asn | Leu | Asn | Lys | Tyr |
| | | | | 600 | | | | | 605 | | | | | 610 | |

| aca | ggt | gtt | ttg | ggt | ctt | ttc | aac | tgc | caa | ggt | ggt | ggg | tgg | tgt | cct | 1987 |
| Thr | Gly | Val | Leu | Gly | Leu | Phe | Asn | Cys | Gln | Gly | Gly | Gly | Trp | Cys | Pro |
| | 615 | | | | | 620 | | | | | 625 | | | | |

| gag | gca | cgg | cga | aac | aag | agt | gta | tct | gaa | ttt | tca | cgc | gcg | gtg | aca | 2035 |
| Glu | Ala | Arg | Arg | Asn | Lys | Ser | Val | Ser | Glu | Phe | Ser | Arg | Ala | Val | Thr |
| 630 | | | | | 635 | | | | | 640 | | | | | 645 |

| tgt | tat | gca | agt | ccc | gaa | gac | att | gaa | tgg | tgc | aat | ggg | aaa | act | cca | 2083 |
| Cys | Tyr | Ala | Ser | Pro | Glu | Asp | Ile | Glu | Trp | Cys | Asn | Gly | Lys | Thr | Pro |
| | | | | 650 | | | | | 655 | | | | | 660 | |

| atg | agc | acc | aaa | ggt | gtg | gat | ttt | ttt | gct | gtg | tat | ttt | ttc | aag | gag | 2131 |
| Met | Ser | Thr | Lys | Gly | Val | Asp | Phe | Phe | Ala | Val | Tyr | Phe | Phe | Lys | Glu |
| | | | 665 | | | | | 670 | | | | | 675 | | |

| aag | aaa | ttg | agg | ctc | atg | aag | tgt | tct | gat | aga | ttg | aaa | gtt | tcg | ctt | 2179 |
| Lys | Lys | Leu | Arg | Leu | Met | Lys | Cys | Ser | Asp | Arg | Leu | Lys | Val | Ser | Leu |
| | | | 680 | | | | | 685 | | | | | 690 | | |

| gag | cca | ttt | agt | ttt | gag | cta | atg | aca | gtg | tct | cca | gtg | aaa | gtg | ttt | 2227 |
| Glu | Pro | Phe | Ser | Phe | Glu | Leu | Met | Thr | Val | Ser | Pro | Val | Lys | Val | Phe |
| 695 | | | | | 700 | | | | | 705 | | | | | |

| tcg | aaa | agg | ttt | ata | cag | ttt | gca | ccg | att | ggg | tta | gtg | aac | atg | ctg | 2275 |
| Ser | Lys | Arg | Phe | Ile | Gln | Phe | Ala | Pro | Ile | Gly | Leu | Val | Asn | Met | Leu |
| 710 | | | | 715 | | | | | 720 | | | | | 725 | |

| aac | tct | ggt | ggt | gcg | att | cag | tct | ctg | gag | ttt | gat | gat | aat | gca | agt | 2323 |
| Asn | Ser | Gly | Gly | Ala | Ile | Gln | Ser | Leu | Glu | Phe | Asp | Asp | Asn | Ala | Ser |
| | | | 730 | | | | | 735 | | | | | 740 | | |

| ttg | gtc | aag | att | ggg | gtg | aga | ggt | tgc | ggg | gag | atg | agc | gtg | ttt | gcg | 2371 |
| Leu | Val | Lys | Ile | Gly | Val | Arg | Gly | Cys | Gly | Glu | Met | Ser | Val | Phe | Ala |
| | | | 745 | | | | | 750 | | | | | 755 | | |

| tct | gag | aaa | ccg | gtt | tgc | tgc | aaa | att | gat | ggg | gtt | aag | gtg | aaa | ttt | 2419 |
| Ser | Glu | Lys | Pro | Val | Cys | Cys | Lys | Ile | Asp | Gly | Val | Lys | Val | Lys | Phe |
| | 760 | | | | | 765 | | | | | 770 | | | | |

| ctt | tat | gag | gac | aaa | atg | gca | aga | gtt | caa | att | ctg | tgg | cct | agt | tct | 2467 |
| Leu | Tyr | Glu | Asp | Lys | Met | Ala | Arg | Val | Gln | Ile | Leu | Trp | Pro | Ser | Ser |
| | 775 | | | | | 780 | | | | | 785 | | | | |

| tca | aca | ttg | tct | ttg | gtc | cag | ttt | tta | ttt | tgatccctag gaatcctatg | 2517 |
| Ser | Thr | Leu | Ser | Leu | Val | Gln | Phe | Leu | Phe |
| 790 | | | | | 795 | | | | | cacgtgtctc tgtttacaag tactttatat aagtataata tgtatctatt tccattttta    2577

-continued

```
actgtctttca tgcaattagg tggtcaatta gttatttgtt tgtgaagtaa ctaacttgct      2637
tgtgttgtaa gcttataata tatggtcaag ttcctcactt gtatatacct gttgtatgta      2697
taaattttac tatatatgac taacatcatt atcttgtgag caaaaaaaa                  2746
```

<210> SEQ ID NO 2
<211> LENGTH: 799
<212> TYPE: PRT
<213> ORGANISM: Vicia faba

<400> SEQUENCE: 2

```
Met Ala Pro Pro Ser Ile Thr Lys Thr Ala Thr Leu Gln Asp Val Ile
 1               5                  10                  15

Ser Thr Ile Asp Ile Gly Asn Gly Asn Ser Pro Leu Phe Ser Ile Thr
                20                  25                  30

Leu Asp Gln Ser Arg Asp Phe Leu Ala Asn Gly His Pro Phe Leu Thr
            35                  40                  45

Gln Val Pro Pro Asn Ile Thr Thr Thr Thr Thr Thr Ala Ser Ser
        50                  55                  60

Phe Leu Asn Leu Lys Ser Asn Lys Asp Thr Ile Pro Asn Asn Asn Asn
 65                  70                  75                  80

Thr Met Leu Leu Gln Gln Gly Cys Phe Val Gly Phe Asn Ser Thr Glu
                85                  90                  95

Pro Lys Ser His His Val Val Pro Leu Gly Lys Leu Lys Gly Ile Lys
            100                 105                 110

Phe Met Ser Ile Phe Arg Phe Lys Val Trp Trp Thr Thr His Trp Val
        115                 120                 125

Gly Thr Asn Gly Gln Glu Leu Gln His Glu Thr Gln Met Leu Ile Leu
    130                 135                 140

Asp Lys Asn Asp Ser Leu Gly Arg Pro Tyr Val Leu Leu Pro Ile
145                 150                 155                 160

Leu Glu Asn Thr Phe Arg Thr Ser Leu Gln Pro Gly Leu Asn Asp His
                165                 170                 175

Ile Gly Met Ser Val Glu Ser Gly Ser Thr His Val Thr Gly Ser Ser
            180                 185                 190

Phe Lys Ala Cys Leu Tyr Ile His Leu Ser Asn Asp Pro Tyr Ser Ile
        195                 200                 205

Leu Lys Glu Ala Val Lys Val Ile Gln Thr Gln Leu Gly Thr Phe Lys
    210                 215                 220

Thr Leu Glu Glu Lys Thr Ala Pro Ser Ile Ile Asp Lys Phe Gly Trp
225                 230                 235                 240

Cys Thr Trp Asp Ala Phe Tyr Leu Lys Val His Pro Lys Gly Val Trp
                245                 250                 255

Glu Gly Val Lys Ser Leu Thr Asp Gly Cys Pro Pro Gly Phe Val
            260                 265                 270

Ile Ile Asp Asp Gly Trp Gln Ser Ile Cys His Asp Asp Asp Glu
        275                 280                 285

Asp Asp Ser Gly Met Asn Arg Thr Ser Ala Gly Glu Gln Met Pro Cys
    290                 295                 300

Arg Leu Val Lys Tyr Glu Glu Asn Ser Lys Phe Arg Glu Tyr Glu Asn
305                 310                 315                 320

Pro Glu Asn Gly Gly Lys Lys Gly Leu Gly Gly Phe Val Arg Asp Leu
                325                 330                 335

Lys Glu Glu Phe Gly Ser Val Glu Ser Val Tyr Val Trp His Ala Leu
```

-continued

```
                  340                 345                 350
    Cys Gly Tyr Trp Gly Gly Val Arg Pro Gly Val His Gly Met Pro Lys
            355                 360                 365
    Ala Arg Val Val Val Pro Lys Val Ser Gln Gly Leu Lys Met Thr Met
        370                 375                 380
    Glu Asp Leu Ala Val Asp Lys Ile Val Glu Asn Gly Val Gly Leu Val
    385                 390                 395                 400
    Pro Pro Asp Phe Ala His Glu Met Phe Asp Gly Leu His Ser His Leu
                    405                 410                 415
    Glu Ser Ala Gly Ile Asp Gly Val Lys Val Asp Val Ile His Leu Leu
                420                 425                 430
    Glu Leu Leu Ser Glu Glu Tyr Gly Gly Arg Val Glu Leu Ala Arg Ala
            435                 440                 445
    Tyr Tyr Lys Ala Leu Thr Ser Ser Val Lys Lys His Phe Lys Gly Asn
        450                 455                 460
    Gly Val Ile Ala Ser Met Glu His Cys Asn Asp Phe Phe Leu Leu Gly
    465                 470                 475                 480
    Thr Glu Ala Ile Ser Leu Gly Arg Val Gly Asp Asp Phe Trp Cys Ser
                    485                 490                 495
    Asp Pro Ser Gly Asp Pro Asn Gly Thr Tyr Trp Leu Gln Gly Cys His
                500                 505                 510
    Met Val His Cys Ala Tyr Asn Ser Leu Trp Met Gly Asn Phe Ile Gln
            515                 520                 525
    Pro Asp Trp Asp Met Phe Gln Ser Thr His Pro Cys Ala Glu Phe His
        530                 535                 540
    Ala Ala Ser Arg Ala Ile Ser Gly Gly Pro Ile Tyr Val Ser Asp Cys
    545                 550                 555                 560
    Val Gly Asn His Asn Phe Lys Leu Leu Lys Ser Leu Val Leu Pro Asp
                    565                 570                 575
    Gly Ser Ile Leu Arg Cys Gln His Tyr Ala Leu Pro Thr Arg Asp Cys
                580                 585                 590
    Leu Phe Glu Asp Pro Leu His Asn Gly Lys Thr Met Leu Lys Ile Trp
            595                 600                 605
    Asn Leu Asn Lys Tyr Thr Gly Val Leu Gly Leu Phe Asn Cys Gln Gly
        610                 615                 620
    Gly Gly Trp Cys Pro Glu Ala Arg Arg Asn Lys Ser Val Ser Glu Phe
    625                 630                 635                 640
    Ser Arg Ala Val Thr Cys Tyr Ala Ser Pro Glu Asp Ile Glu Trp Cys
                    645                 650                 655
    Asn Gly Lys Thr Pro Met Ser Thr Lys Gly Val Asp Phe Phe Ala Val
                660                 665                 670
    Tyr Phe Phe Lys Glu Lys Lys Leu Arg Leu Met Lys Cys Ser Asp Arg
            675                 680                 685
    Leu Lys Val Ser Leu Glu Pro Phe Ser Phe Glu Leu Met Thr Val Ser
        690                 695                 700
    Pro Val Lys Val Phe Ser Lys Arg Phe Ile Gln Phe Ala Pro Ile Gly
    705                 710                 715                 720
    Leu Val Asn Met Leu Asn Ser Gly Gly Ala Ile Gln Ser Leu Glu Phe
                    725                 730                 735
    Asp Asp Asn Ala Ser Leu Val Lys Ile Gly Val Arg Gly Cys Gly Glu
                740                 745                 750
    Met Ser Val Phe Ala Ser Glu Lys Pro Val Cys Cys Lys Ile Asp Gly
            755                 760                 765
```

```
Val Lys Val Lys Phe Leu Tyr Glu Asp Lys Met Ala Arg Val Gln Ile
        770                 775                 780

Leu Trp Pro Ser Ser Ser Thr Leu Ser Leu Val Gln Phe Leu Phe
785                 790                 795

<210> SEQ ID NO 3
<211> LENGTH: 2498
<212> TYPE: DNA
<213> ORGANISM: Glycine max
<220> FEATURE:
<221> NAME/KEY: CDS
<222> LOCATION: (62)..(2404)

<400> SEQUENCE: 3
ccaaaccata gcaaacctaa gcaccaaacc tctttcttc aagatccttg aattcagtcc         60 c atg gct cca agc ata agc aaa act gtg gaa cta aat tca ttt ggt ctt       109
  Met Ala Pro Ser Ile Ser Lys Thr Val Glu Leu Asn Ser Phe Gly Leu
  1               5                   10                  15 gtc aac ggt aat ttg cct ttg tcc ata acc cta gaa gga tca aat ttc         157
Val Asn Gly Asn Leu Pro Leu Ser Ile Thr Leu Glu Gly Ser Asn Phe
                20                  25                  30 ctc gcc aac ggc cac cct ttt ctc acg gaa gtt ccc gaa aac ata ata         205
Leu Ala Asn Gly His Pro Phe Leu Thr Glu Val Pro Glu Asn Ile Ile
        35                  40                  45 gtc acc cct tca ccc atc gac gcc aag agt agt aag aac aac gag gac         253
Val Thr Pro Ser Pro Ile Asp Ala Lys Ser Ser Lys Asn Asn Glu Asp
    50                  55                  60 gac gac gtc gta ggt tgc ttc gtg ggc ttc cac gcg gac gag ccc aga         301
Asp Asp Val Val Gly Cys Phe Val Gly Phe His Ala Asp Glu Pro Arg
65                  70                  75                  80 agc cga cac gtg gct tcc ctg ggg aag ctc aga gga ata aaa ttc atg         349
Ser Arg His Val Ala Ser Leu Gly Lys Leu Arg Gly Ile Lys Phe Met
                85                  90                  95 agc ata ttc cgg ttt aag gtg tgg tgg acc act cac tgg gtc ggt agc         397
Ser Ile Phe Arg Phe Lys Val Trp Trp Thr Thr His Trp Val Gly Ser
                100                 105                 110 aac gga cac gaa ctg gag cac gag aca cag atg atg ctt ctc gac aaa         445
Asn Gly His Glu Leu Glu His Glu Thr Gln Met Met Leu Leu Asp Lys
        115                 120                 125 aac gac cag ctc gga cgc ccc ttt gtg ttg att ctc ccg atc ctc caa         493
Asn Asp Gln Leu Gly Arg Pro Phe Val Leu Ile Leu Pro Ile Leu Gln
    130                 135                 140 gcc tcg ttc cga gcc tcc ctg caa ccc ggt ttg gat gat tac gtg gac         541
Ala Ser Phe Arg Ala Ser Leu Gln Pro Gly Leu Asp Asp Tyr Val Asp
145                 150                 155                 160 gtt tgc atg gag agc ggg tcg aca cgt gtc tgt ggc tcc agc ttc ggg         589
Val Cys Met Glu Ser Gly Ser Thr Arg Val Cys Gly Ser Ser Phe Gly
                165                 170                 175 agc tgc tta tac gtc cac gtt ggc cat gac ccg tat cag ttg ctt aga         637
Ser Cys Leu Tyr Val His Val Gly His Asp Pro Tyr Gln Leu Leu Arg
                180                 185                 190 gaa gca act aaa gtc gtt agg atg cat ttg ggg acg ttc aag ctt ctc         685
Glu Ala Thr Lys Val Val Arg Met His Leu Gly Thr Phe Lys Leu Leu
        195                 200                 205 gag gag aaa acc gcg cca gtg atc ata gac aag ttt ggt tgg tgt aca         733
Glu Glu Lys Thr Ala Pro Val Ile Ile Asp Lys Phe Gly Trp Cys Thr
    210                 215                 220 tgg gac gcg ttt tac ttg aag gtg cat ccc tca ggt gtg tgg gaa ggg         781
Trp Asp Ala Phe Tyr Leu Lys Val His Pro Ser Gly Val Trp Glu Gly
225                 230                 235                 240
```

-continued

| | |
|---|---|
| gtg aaa ggg ttg gtg gag gga ggg tgc cct cca ggg atg gtc cta atc<br>Val Lys Gly Leu Val Glu Gly Gly Cys Pro Pro Gly Met Val Leu Ile<br>                   245                   250               255 | 829 |
| gac gac ggg tgg caa gcc att tgt cac gac gag gac ccc ata acg gac<br>Asp Asp Gly Trp Gln Ala Ile Cys His Asp Glu Asp Pro Ile Thr Asp<br>                 260                   265               270 | 877 |
| caa gag ggt atg aag cga acc tcc gca ggg gag caa atg cca tgc agg<br>Gln Glu Gly Met Lys Arg Thr Ser Ala Gly Glu Gln Met Pro Cys Arg<br>           275                   280               285 | 925 |
| ttg gtg aag ttg gag gaa aat tac aag ttc aga cag tat tgt agt gga<br>Leu Val Lys Leu Glu Glu Asn Tyr Lys Phe Arg Gln Tyr Cys Ser Gly<br>290                 295               300 | 973 |
| aag gat tct gag aag ggt atg ggt gcc ttt gtt agg gac ttg aag gaa<br>Lys Asp Ser Glu Lys Gly Met Gly Ala Phe Val Arg Asp Leu Lys Glu<br>305                 310               315              320 | 1021 |
| cag ttt agg agc gtg gag cag gtg tat gtg tgg cac gcg ctt tgt ggg<br>Gln Phe Arg Ser Val Glu Gln Val Tyr Val Trp His Ala Leu Cys Gly<br>                 325                   330               335 | 1069 |
| tat tgg ggt ggg gtc aga ccc aag gtt ccg ggc atg ccc cag gct aag<br>Tyr Trp Gly Gly Val Arg Pro Lys Val Pro Gly Met Pro Gln Ala Lys<br>           340                   345               350 | 1117 |
| gtt gtc act ccg aag ctg tcc aat gga cta aaa ttg aca atg aag gat<br>Val Val Thr Pro Lys Leu Ser Asn Gly Leu Lys Leu Thr Met Lys Asp<br>                 355                   360               365 | 1165 |
| tta gcg gtg gat aag atc gtc agt aac gga gtt gga ctg gtg cca cca<br>Leu Ala Val Asp Lys Ile Val Ser Asn Gly Val Gly Leu Val Pro Pro<br>370                 375               380 | 1213 |
| cac ctg gct cac ctt ttg tac gag ggg ctc cac tcc cgt ttg gaa tct<br>His Leu Ala His Leu Leu Tyr Glu Gly Leu His Ser Arg Leu Glu Ser<br>385                 390               395              400 | 1261 |
| gcg ggt att gac ggt gtt aag gtt gac gtt ata cac ttg ctc gag atg<br>Ala Gly Ile Asp Gly Val Lys Val Asp Val Ile His Leu Leu Glu Met<br>                     405                   410               415 | 1309 |
| cta tcc gag gaa tac ggt ggc cgt gtt gag cta gcc aaa gct tat tac<br>Leu Ser Glu Glu Tyr Gly Gly Arg Val Glu Leu Ala Lys Ala Tyr Tyr<br>           420                   425               430 | 1357 |
| aaa gcg ctc act gct tcg gtg aag aag cat ttc aaa ggc aat ggg gtc<br>Lys Ala Leu Thr Ala Ser Val Lys Lys His Phe Lys Gly Asn Gly Val<br>                 435                   440               445 | 1405 |
| att gcg agc atg gag cat tgt aat gac ttc ttt ctc ctt ggt acc gaa<br>Ile Ala Ser Met Glu His Cys Asn Asp Phe Phe Leu Leu Gly Thr Glu<br>           450                   455               460 | 1453 |
| gcc ata gcc ctt ggg cgc gta gga gat gat ttt tgg tgc act gat ccc<br>Ala Ile Ala Leu Gly Arg Val Gly Asp Asp Phe Trp Cys Thr Asp Pro<br>465                 470               475              480 | 1501 |
| tct gga gat cca aat ggc acg tat tgg ctc caa ggg tgt cac atg gtg<br>Ser Gly Asp Pro Asn Gly Thr Tyr Trp Leu Gln Gly Cys His Met Val<br>                 485                   490               495 | 1549 |
| cac tgt gcc tac aac agc ttg tgg atg ggg aat ttt att cag ccg gat<br>His Cys Ala Tyr Asn Ser Leu Trp Met Gly Asn Phe Ile Gln Pro Asp<br>           500                   505               510 | 1597 |
| tgg gac atg ttc cag tcc act cac cct tgt gcc gaa ttc cat gcn gcc<br>Trp Asp Met Phe Gln Ser Thr His Pro Cys Ala Glu Phe His Ala Ala<br>                 515                   520               525 | 1645 |
| tct agg gcc atc tct ggt gga cca gtt tac gtt agt gat tgt gtt gga<br>Ser Arg Ala Ile Ser Gly Gly Pro Val Tyr Val Ser Asp Cys Val Gly<br>530                 535               540 | 1693 |
| aag cac aac ttc aag ttg ctc aag agc ctc gct ttg cct gat ggg acg<br>Lys His Asn Phe Lys Leu Leu Lys Ser Leu Ala Leu Pro Asp Gly Thr | 1741 |

```
                      545                 550                 555                 560
att ttg cgt tgt caa cac tat gca ctc ccc aca cga gac tgt ttg ttt                   1789
Ile Leu Arg Cys Gln His Tyr Ala Leu Pro Thr Arg Asp Cys Leu Phe
                565                 570                 575 gaa gac ccc ttg cat gat ggg aag aca atg ctc aaa att tgg aat ctc                   1837
Glu Asp Pro Leu His Asp Gly Lys Thr Met Leu Lys Ile Trp Asn Leu
            580                 585                 590 aac aaa tat aca ggt gtt ttg ggt cta ttt aat tgc caa gga ggt ggg                   1885
Asn Lys Tyr Thr Gly Val Leu Gly Leu Phe Asn Cys Gln Gly Gly Gly
        595                 600                 605 tgg tgt ccc gta act agg aga aac aag agt gcc tct gaa ttt tca caa                   1933
Trp Cys Pro Val Thr Arg Arg Asn Lys Ser Ala Ser Glu Phe Ser Gln
    610                 615                 620 act gtg aca tgc tta gcg agt cct caa gac att gaa tgg agc aat ggg                   1981
Thr Val Thr Cys Leu Ala Ser Pro Gln Asp Ile Glu Trp Ser Asn Gly
625                 630                 635                 640 aaa agc cca ata tgc ata aaa ggg atg aat gtg ttt gct gta tat ttg                   2029
Lys Ser Pro Ile Cys Ile Lys Gly Met Asn Val Phe Ala Val Tyr Leu
                645                 650                 655 ttc aag gac cac aaa cta aag ctc atg aag gca tca gag aaa ttg gaa                   2077
Phe Lys Asp His Lys Leu Lys Leu Met Lys Ala Ser Glu Lys Leu Glu
            660                 665                 670 gtt tca ctt gag cca ttt act ttt gag cta ttg aca gtg tct cca gtg                   2125
Val Ser Leu Glu Pro Phe Thr Phe Glu Leu Leu Thr Val Ser Pro Val
        675                 680                 685 att gtg ctg tca aaa aag tta att caa ttt gct cca att gga tta gtg                   2173
Ile Val Leu Ser Lys Lys Leu Ile Gln Phe Ala Pro Ile Gly Leu Val
    690                 695                 700 aac atg ctt aac act ggt ggt gcc att cag tcc atg gag ttt gac aac                   2221
Asn Met Leu Asn Thr Gly Gly Ala Ile Gln Ser Met Glu Phe Asp Asn
705                 710                 715                 720 cac ata gat gtg gtc aaa att ggg gtt agg ggt tgt ggg gag atg aag                   2269
His Ile Asp Val Val Lys Ile Gly Val Arg Gly Cys Gly Glu Met Lys
                725                 730                 735 gtg ttt gca tca gag aaa cca gtt agt tgc aaa cta gat ggg gta gtt                   2317
Val Phe Ala Ser Glu Lys Pro Val Ser Cys Lys Leu Asp Gly Val Val
            740                 745                 750 gta aaa ttt gat tat gag gat aaa atg ctg aga gtg caa gtt ccc tgg                   2365
Val Lys Phe Asp Tyr Glu Asp Lys Met Leu Arg Val Gln Val Pro Trp
        755                 760                 765 cct agt gct tca aaa ttg tca atg gtt gag ttt tta ttt tgatccctga                    2414
Pro Ser Ala Ser Lys Leu Ser Met Val Glu Phe Leu Phe
    770                 775                 780 aggtgaattt gggatactat gatgtttgac tctctttta agtaataaga gtcatatttt                  2474
tctgttgtaa aaaaaaaaaa aaaa                                                        2498

<210> SEQ ID NO 4
<211> LENGTH: 781
<212> TYPE: PRT
<213> ORGANISM: Glycine max

<400> SEQUENCE: 4

Met Ala Pro Ser Ile Ser Lys Thr Val Glu Leu Asn Ser Phe Gly Leu
  1               5                  10                  15

Val Asn Gly Asn Leu Pro Leu Ser Ile Thr Leu Glu Gly Ser Asn Phe
             20                  25                  30

Leu Ala Asn Gly His Pro Phe Leu Thr Glu Val Pro Glu Asn Ile Ile
         35                  40                  45
```

-continued

```
Val Thr Pro Ser Pro Ile Asp Ala Lys Ser Lys Asn Asn Glu Asp
    50                  55                  60

Asp Asp Val Val Gly Cys Phe Val Gly Phe His Ala Asp Glu Pro Arg
65              70                  75                  80

Ser Arg His Val Ala Ser Leu Gly Lys Leu Arg Gly Ile Lys Phe Met
                85                  90                  95

Ser Ile Phe Arg Phe Lys Val Trp Trp Thr Thr His Trp Val Gly Ser
            100                 105                 110

Asn Gly His Glu Leu Glu His Glu Thr Gln Met Met Leu Leu Asp Lys
        115                 120                 125

Asn Asp Gln Leu Gly Arg Pro Phe Val Leu Ile Leu Pro Ile Leu Gln
    130                 135                 140

Ala Ser Phe Arg Ala Ser Leu Gln Pro Gly Leu Asp Asp Tyr Val Asp
145                 150                 155                 160

Val Cys Met Glu Ser Gly Ser Thr Arg Val Cys Gly Ser Ser Phe Gly
                165                 170                 175

Ser Cys Leu Tyr Val His Val Gly His Asp Pro Tyr Gln Leu Leu Arg
            180                 185                 190

Glu Ala Thr Lys Val Val Arg Met His Leu Gly Thr Phe Lys Leu Leu
        195                 200                 205

Glu Glu Lys Thr Ala Pro Val Ile Ile Asp Lys Phe Gly Trp Cys Thr
    210                 215                 220

Trp Asp Ala Phe Tyr Leu Lys Val His Pro Ser Gly Val Trp Glu Gly
225                 230                 235                 240

Val Lys Gly Leu Val Glu Gly Gly Cys Pro Pro Gly Met Val Leu Ile
                245                 250                 255

Asp Asp Gly Trp Gln Ala Ile Cys His Asp Glu Asp Pro Ile Thr Asp
            260                 265                 270

Gln Glu Gly Met Lys Arg Thr Ser Ala Gly Glu Gln Met Pro Cys Arg
        275                 280                 285

Leu Val Lys Leu Glu Glu Asn Tyr Lys Phe Arg Gln Tyr Cys Ser Gly
    290                 295                 300

Lys Asp Ser Glu Lys Gly Met Gly Ala Phe Val Arg Asp Leu Lys Glu
305                 310                 315                 320

Gln Phe Arg Ser Val Glu Gln Val Tyr Val Trp His Ala Leu Cys Gly
                325                 330                 335

Tyr Trp Gly Gly Val Arg Pro Lys Val Pro Gly Met Pro Gln Ala Lys
            340                 345                 350

Val Val Thr Pro Lys Leu Ser Asn Gly Leu Lys Leu Thr Met Lys Asp
        355                 360                 365

Leu Ala Val Asp Lys Ile Val Ser Asn Gly Val Gly Leu Val Pro Pro
    370                 375                 380

His Leu Ala His Leu Leu Tyr Glu Gly Leu His Ser Arg Leu Glu Ser
385                 390                 395                 400

Ala Gly Ile Asp Gly Val Lys Val Asp Val Ile His Leu Leu Glu Met
                405                 410                 415

Leu Ser Glu Glu Tyr Gly Gly Arg Val Glu Leu Ala Lys Ala Tyr Tyr
            420                 425                 430

Lys Ala Leu Thr Ala Ser Val Lys Lys His Phe Lys Gly Asn Gly Val
        435                 440                 445

Ile Ala Ser Met Glu His Cys Asn Asp Phe Phe Leu Leu Gly Thr Glu
    450                 455                 460

Ala Ile Ala Leu Gly Arg Val Gly Asp Asp Phe Trp Cys Thr Asp Pro
```

-continued

```
                465                 470                 475                 480
        Ser Gly Asp Pro Asn Gly Thr Tyr Trp Leu Gln Gly Cys His Met Val
                        485                 490                 495

His Cys Ala Tyr Asn Ser Leu Trp Met Gly Asn Phe Ile Gln Pro Asp
                        500                 505                 510

Trp Asp Met Phe Gln Ser Thr His Pro Cys Ala Glu Phe His Ala Ala
                        515                 520                 525

Ser Arg Ala Ile Ser Gly Gly Pro Val Tyr Val Ser Asp Cys Val Gly
                        530                 535                 540

Lys His Asn Phe Lys Leu Leu Lys Ser Leu Ala Leu Pro Asp Gly Thr
        545                 550                 555                 560

Ile Leu Arg Cys Gln His Tyr Ala Leu Pro Thr Arg Asp Cys Leu Phe
                        565                 570                 575

Glu Asp Pro Leu His Asp Gly Lys Thr Met Leu Lys Ile Trp Asn Leu
                        580                 585                 590

Asn Lys Tyr Thr Gly Val Leu Gly Leu Phe Asn Cys Gln Gly Gly Gly
                        595                 600                 605

Trp Cys Pro Val Thr Arg Arg Asn Lys Ser Ala Ser Glu Phe Ser Gln
                        610                 615                 620

Thr Val Thr Cys Leu Ala Ser Pro Gln Asp Ile Glu Trp Ser Asn Gly
        625                 630                 635                 640

Lys Ser Pro Ile Cys Ile Lys Gly Met Asn Val Phe Ala Val Tyr Leu
                        645                 650                 655

Phe Lys Asp His Lys Leu Lys Leu Met Lys Ala Ser Glu Lys Leu Glu
                        660                 665                 670

Val Ser Leu Glu Pro Phe Thr Phe Glu Leu Leu Thr Val Ser Pro Val
                        675                 680                 685

Ile Val Leu Ser Lys Lys Leu Ile Gln Phe Ala Pro Ile Gly Leu Val
                        690                 695                 700

Asn Met Leu Asn Thr Gly Gly Ala Ile Gln Ser Met Glu Phe Asp Asn
        705                 710                 715                 720

His Ile Asp Val Val Lys Ile Gly Val Arg Gly Cys Gly Glu Met Lys
                        725                 730                 735

Val Phe Ala Ser Glu Lys Pro Val Ser Cys Lys Leu Asp Gly Val Val
                        740                 745                 750

Val Lys Phe Asp Tyr Glu Asp Lys Met Leu Arg Val Gln Val Pro Trp
                        755                 760                 765

Pro Ser Ala Ser Lys Leu Ser Met Val Glu Phe Leu Phe
                        770                 775                 780

<210> SEQ ID NO 5
<211> LENGTH: 1762
<212> TYPE: DNA
<213> ORGANISM: Stachys sieboldii
<220> FEATURE:
<221> NAME/KEY: CDS
<222> LOCATION: (2)..(1759)

<400> SEQUENCE: 5 g aca aac ggg tcg gat ctt gag cgg gaa act caa ata gtc gtg ctc gac      49
  Thr Asn Gly Ser Asp Leu Glu Arg Glu Thr Gln Ile Val Val Leu Asp
    1               5                  10                  15 aag tcc gac gac agg ccc tac atc gtg ctg ctt ccg ctc atc gag ggg       97
Lys Ser Asp Asp Arg Pro Tyr Ile Val Leu Leu Pro Leu Ile Glu Gly
            20                  25                  30 cag ttt cgg gct tcc ctt cag ccc ggt gtg gat gat ttt atc gat att      145
```

```
                Gln Phe Arg Ala Ser Leu Gln Pro Gly Val Asp Asp Phe Ile Asp Ile
                             35                  40                  45 tgt gtc gaa agc ggg tca acc aag gtc aac gag tcc tcg ttc cgt gct         193
Cys Val Glu Ser Gly Ser Thr Lys Val Asn Glu Ser Ser Phe Arg Ala
 50                  55                  60 tcg ctc tac atg cac gcc ggt gat gac cct ttt acc ctg gtg aag gac         241
Ser Leu Tyr Met His Ala Gly Asp Asp Pro Phe Thr Leu Val Lys Asp
 65                  70                  75                  80 gcc gtg aag gtg gcg cgc cac cac ctc ggg acg ttc agg ctg ctg gag         289
Ala Val Lys Val Ala Arg His His Leu Gly Thr Phe Arg Leu Leu Glu
                 85                  90                  95 gag aaa act ccg ccg ggg atc gtc gac aaa ttc ggg tgg tgc acg tgg         337
Glu Lys Thr Pro Pro Gly Ile Val Asp Lys Phe Gly Trp Cys Thr Trp
            100                 105                 110 gat gcg ttc tac ctc aac gtc cag ccc cac ggc gtt atg gag ggc gtg         385
Asp Ala Phe Tyr Leu Asn Val Gln Pro His Gly Val Met Glu Gly Val
        115                 120                 125 cag ggg ctg gtt gac ggc gga tgt ccg ggg ctg gtg ttg atc gac             433
Gln Gly Leu Val Asp Gly Gly Cys Pro Gly Leu Val Leu Ile Asp
    130                 135                 140 gac ggg tgg cag tcc att tgt cac gac aac gac gcg ctc acc acc gag         481
Asp Gly Trp Gln Ser Ile Cys His Asp Asn Asp Ala Leu Thr Thr Glu
145                 150                 155                 160 ggg atg ggg aga acc tcc gcc gga gag caa atg ccc tgc agg ttg atc         529
Gly Met Gly Arg Thr Ser Ala Gly Glu Gln Met Pro Cys Arg Leu Ile
                165                 170                 175 aag ttt gag gag aat tac aag ttc agg gag tac gag agc ccg aat aaa         577
Lys Phe Glu Glu Asn Tyr Lys Phe Arg Glu Tyr Glu Ser Pro Asn Lys
            180                 185                 190 act ggg ccg ggc ccg aat acg ggg atg ggg gcc ttt att cgt gac atg         625
Thr Gly Pro Gly Pro Asn Thr Gly Met Gly Ala Phe Ile Arg Asp Met
        195                 200                 205 aag gac aat ttc aag agt gtg gac tac gtg tac gtg tgg cat gcg ttg         673
Lys Asp Asn Phe Lys Ser Val Asp Tyr Val Tyr Val Trp His Ala Leu
    210                 215                 220 tgt ggt tat tgg ggc ggg ctc agg ccc aat gtt ccg ggc ctg ccc gag         721
Cys Gly Tyr Trp Gly Gly Leu Arg Pro Asn Val Pro Gly Leu Pro Glu
225                 230                 235                 240 gct aag ctc att gag ccc aaa ctg act cct ggg ctt aag acc acc atg         769
Ala Lys Leu Ile Glu Pro Lys Leu Thr Pro Gly Leu Lys Thr Thr Met
                245                 250                 255 gaa gat ttg gct gtt gat aag att gtc aac aat ggc gtg ggt ctg gtc         817
Glu Asp Leu Ala Val Asp Lys Ile Val Asn Asn Gly Val Gly Leu Val
            260                 265                 270 cca ccg gag ttt gtt gaa caa atg tat gaa gga tta cat tca cat ctc         865
Pro Pro Glu Phe Val Glu Gln Met Tyr Glu Gly Leu His Ser His Leu
        275                 280                 285 gaa tct gtg ggg att gat gga gtc aaa gtt gac gtc atc cat ttg ttg         913
Glu Ser Val Gly Ile Asp Gly Val Lys Val Asp Val Ile His Leu Leu
    290                 295                 300 gaa atg ttg tgt gaa gac tat ggt ggg aga gtg gac tta gcc aag gct         961
Glu Met Leu Cys Glu Asp Tyr Gly Gly Arg Val Asp Leu Ala Lys Ala
305                 310                 315                 320 tat tac aag gcc tta tca agc tca gtt aac aac cac ttc aac ggc aac        1009
Tyr Tyr Lys Ala Leu Ser Ser Ser Val Asn Asn His Phe Asn Gly Asn
                325                 330                 335 ggc gtc atc gct ggc ctg gag cac tgc aat gac ttc atg ttt ctc gga        1057
Gly Val Ile Ala Gly Leu Glu His Cys Asn Asp Phe Met Phe Leu Gly
            340                 345                 350
```

-continued

```
acc gag gcc att acc ttg ggt cgt gtc ggg gat gat ttt tgg tgc act    1105
Thr Glu Ala Ile Thr Leu Gly Arg Val Gly Asp Asp Phe Trp Cys Thr
            355                 360                 365 gat cca tct gga gat ccc aat ggc acg ttc tgg ttg caa ggg tgt cac    1153
Asp Pro Ser Gly Asp Pro Asn Gly Thr Phe Trp Leu Gln Gly Cys His
    370                 375                 380 atg gtg cac tgc gcc tac aac agc ata tgg atg ggt aat ttc atc cac    1201
Met Val His Cys Ala Tyr Asn Ser Ile Trp Met Gly Asn Phe Ile His
385                 390                 395                 400 cct gat tgg gac atg ttt caa tcg act cac cct tgc gct gaa ttc cac    1249
Pro Asp Trp Asp Met Phe Gln Ser Thr His Pro Cys Ala Glu Phe His
                405                 410                 415 gct gcc tca cga gcc atc tcc ggc ggg ccc att tac gtc agt gac tcg    1297
Ala Ala Ser Arg Ala Ile Ser Gly Gly Pro Ile Tyr Val Ser Asp Ser
            420                 425                 430 gtc gga aag cac aac ttc gag ctc ctt agg agc ctc gtt ctt ccc gat    1345
Val Gly Lys His Asn Phe Glu Leu Leu Arg Ser Leu Val Leu Pro Asp
        435                 440                 445 ggc tcc atc ctc cgt tgt gat tac tac gcg ctt ccg act cgc gat tgc    1393
Gly Ser Ile Leu Arg Cys Asp Tyr Tyr Ala Leu Pro Thr Arg Asp Cys
    450                 455                 460 ctc ttt gaa gat cca ctt cac aat ggc aag act atg ctc aaa att tgg    1441
Leu Phe Glu Asp Pro Leu His Asn Gly Lys Thr Met Leu Lys Ile Trp
465                 470                 475                 480 aat tat aac aag ttc acc gga gtt gtc gga act ttc aac tgc caa ggt    1489
Asn Tyr Asn Lys Phe Thr Gly Val Val Gly Thr Phe Asn Cys Gln Gly
                485                 490                 495 ggc ggg tgg agc cgg gaa gtg cgt cgc aac caa tgc gct gcc gag tat    1537
Gly Gly Trp Ser Arg Glu Val Arg Arg Asn Gln Cys Ala Ala Glu Tyr
            500                 505                 510 tcc cac gcc gtc tcc tct agc gct ggt ccg agt gac att gag tgg aag    1585
Ser His Ala Val Ser Ser Ser Ala Gly Pro Ser Asp Ile Glu Trp Lys
        515                 520                 525 caa gga acg agt ccg atc gac gtc gac ggc gtc aaa aca ttc gcg ttg    1633
Gln Gly Thr Ser Pro Ile Asp Val Asp Gly Val Lys Thr Phe Ala Leu
    530                 535                 540 tac cta ttc cac gag aag aaa ctc gtc ctt tct aag cca tca gac aaa    1681
Tyr Leu Phe His Glu Lys Lys Leu Val Leu Ser Lys Pro Ser Asp Lys
545                 550                 555                 560 atc gac atc acg ctt gag ccc ttc gat ttt gag ctg ata acc gtt tct    1729
Ile Asp Ile Thr Leu Glu Pro Phe Asp Phe Glu Leu Ile Thr Val Ser
                565                 570                 575 cca gtc aaa act cta gcc aat tgc acc gtc caa                        1762
Pro Val Lys Thr Leu Ala Asn Cys Thr Val Gln
            580                 585

<210> SEQ ID NO 6
<211> LENGTH: 586
<212> TYPE: PRT
<213> ORGANISM: Stachys sieboldii

<400> SEQUENCE: 6

Thr Asn Gly Ser Asp Leu Glu Arg Glu Thr Gln Ile Val Val Leu Asp
1               5                   10                  15

Lys Ser Asp Asp Arg Pro Tyr Ile Val Leu Leu Pro Leu Ile Glu Gly
                20                  25                  30

Gln Phe Arg Ala Ser Leu Gln Pro Gly Val Asp Asp Phe Ile Asp Ile
            35                  40                  45

Cys Val Glu Ser Gly Ser Thr Lys Val Asn Glu Ser Ser Phe Arg Ala
        50                  55                  60
```

-continued

```
Ser Leu Tyr Met His Ala Gly Asp Asp Pro Phe Thr Leu Val Lys Asp
 65                  70                  75                  80

Ala Val Lys Val Ala Arg His His Leu Gly Thr Phe Arg Leu Leu Glu
                 85                  90                  95

Glu Lys Thr Pro Pro Gly Ile Val Asp Lys Phe Gly Trp Cys Thr Trp
            100                 105                 110

Asp Ala Phe Tyr Leu Asn Val Gln Pro His Gly Val Met Glu Gly Val
        115                 120                 125

Gln Gly Leu Val Asp Gly Gly Cys Pro Pro Gly Leu Val Leu Ile Asp
    130                 135                 140

Asp Gly Trp Gln Ser Ile Cys His Asp Asn Asp Ala Leu Thr Thr Glu
145                 150                 155                 160

Gly Met Gly Arg Thr Ser Ala Gly Glu Gln Met Pro Cys Arg Leu Ile
                165                 170                 175

Lys Phe Glu Glu Asn Tyr Lys Phe Arg Glu Tyr Glu Ser Pro Asn Lys
            180                 185                 190

Thr Gly Pro Gly Pro Asn Thr Gly Met Gly Ala Phe Ile Arg Asp Met
        195                 200                 205

Lys Asp Asn Phe Lys Ser Val Asp Tyr Val Tyr Val Trp His Ala Leu
    210                 215                 220

Cys Gly Tyr Trp Gly Gly Leu Arg Pro Asn Val Pro Gly Leu Pro Glu
225                 230                 235                 240

Ala Lys Leu Ile Glu Pro Lys Leu Thr Pro Gly Leu Lys Thr Thr Met
                245                 250                 255

Glu Asp Leu Ala Val Asp Lys Ile Val Asn Asn Gly Val Gly Leu Val
            260                 265                 270

Pro Pro Glu Phe Val Glu Gln Met Tyr Glu Gly Leu His Ser His Leu
        275                 280                 285

Glu Ser Val Gly Ile Asp Gly Val Lys Val Asp Val Ile His Leu Leu
    290                 295                 300

Glu Met Leu Cys Glu Asp Tyr Gly Gly Arg Val Asp Leu Ala Lys Ala
305                 310                 315                 320

Tyr Tyr Lys Ala Leu Ser Ser Val Asn Asn His Phe Asn Gly Asn
                325                 330                 335

Gly Val Ile Ala Gly Leu Glu His Cys Asn Asp Phe Met Phe Leu Gly
            340                 345                 350

Thr Glu Ala Ile Thr Leu Gly Arg Val Gly Asp Asp Phe Trp Cys Thr
        355                 360                 365

Asp Pro Ser Gly Asp Pro Asn Gly Thr Phe Trp Leu Gln Gly Cys His
    370                 375                 380

Met Val His Cys Ala Tyr Asn Ser Ile Trp Met Gly Asn Phe Ile His
385                 390                 395                 400

Pro Asp Trp Asp Met Phe Gln Ser Thr His Pro Cys Ala Glu Phe His
                405                 410                 415

Ala Ala Ser Arg Ala Ile Ser Gly Gly Pro Ile Tyr Val Ser Asp Ser
            420                 425                 430

Val Gly Lys His Asn Phe Glu Leu Leu Arg Ser Leu Val Leu Pro Asp
        435                 440                 445

Gly Ser Ile Leu Arg Cys Asp Tyr Tyr Ala Leu Pro Thr Arg Asp Cys
    450                 455                 460

Leu Phe Glu Asp Pro Leu His Asn Gly Lys Thr Met Leu Lys Ile Trp
465                 470                 475                 480
```

```
                Asn Tyr Asn Lys Phe Thr Gly Val Val Gly Thr Phe Asn Cys Gln Gly
                                485                 490                 495

Gly Gly Trp Ser Arg Glu Val Arg Arg Asn Gln Cys Ala Ala Glu Tyr
                            500                 505                 510

Ser His Ala Val Ser Ser Ala Gly Pro Ser Asp Ile Glu Trp Lys
                            515                 520                 525

Gln Gly Thr Ser Pro Ile Asp Val Asp Gly Val Lys Thr Phe Ala Leu
                            530                 535                 540

Tyr Leu Phe His Glu Lys Lys Leu Val Leu Ser Lys Pro Ser Asp Lys
                545                 550                 555                 560

Ile Asp Ile Thr Leu Glu Pro Phe Asp Phe Glu Leu Ile Thr Val Ser
                                565                 570                 575

Pro Val Lys Thr Leu Ala Asn Cys Thr Val
                            580                 585

<210> SEQ ID NO 7
<211> LENGTH: 993
<212> TYPE: DNA
<213> ORGANISM: Zea mays
<220> FEATURE:
<221> NAME/KEY: CDS
<222> LOCATION: (2)..(814)

<400> SEQUENCE: 7 c cag tcc acg cac ccc tgc gcc gcc ttc cac gcc gcg tcc cgc gcc atc        49
  Gln Ser Thr His Pro Cys Ala Ala Phe His Ala Ala Ser Arg Ala Ile
    1               5                  10                  15 tcc ggc ggg ccc atc tac gtc agc gac tcg gtg ggg cag cac gac ttc        97
Ser Gly Gly Pro Ile Tyr Val Ser Asp Ser Val Gly Gln His Asp Phe
                20                  25                  30 gcg ctg ctc cgc cgc ctg gcg ctc ccc gac ggc acc gtc ctc cgg tgc       145
Ala Leu Leu Arg Arg Leu Ala Leu Pro Asp Gly Thr Val Leu Arg Cys
            35                  40                  45 gag ggc cac gcg ctg ccc acg cgc gac tgc ctc ttc gcc gac ccg ctc       193
Glu Gly His Ala Leu Pro Thr Arg Asp Cys Leu Phe Ala Asp Pro Leu
        50                  55                  60 cac gac ggc cgg acc gtg ctc aag atc tgg aac gtg aac cgc ttc gcc       241
His Asp Gly Arg Thr Val Leu Lys Ile Trp Asn Val Asn Arg Phe Ala
 65                  70                  75                  80 ggc gtc gtc ggc gcc ttc aac tgc cag ggc ggc ggg tgg agc ccc gag       289
Gly Val Val Gly Ala Phe Asn Cys Gln Gly Gly Gly Trp Ser Pro Glu
                 85                  90                  95 gcg cgg cgg aac aag tgc ttc tcg gag ttc tcc gtg ccc ctg gcc gcg       337
Ala Arg Arg Asn Lys Cys Phe Ser Glu Phe Ser Val Pro Leu Ala Ala
            100                 105                 110 cgc gcc tcg ccg tcc gac gtc gag tgg aag agc ggc aag gcg ggg cca       385
Arg Ala Ser Pro Ser Asp Val Glu Trp Lys Ser Gly Lys Ala Gly Pro
        115                 120                 125 ggc gtc agc gtc aag gac gtc tcc cag ttc gcc gtg tac gcg gtc gag       433
Gly Val Ser Val Lys Asp Val Ser Gln Phe Ala Val Tyr Ala Val Glu
    130                 135                 140 gcc agg acg ctg cag ctg ctg cgc ccc gac gag ggc gtc gac ctc acg       481
Ala Arg Thr Leu Gln Leu Leu Arg Pro Asp Glu Gly Val Asp Leu Thr
145                 150                 155                 160 ctg cag ccc ttc acc tac gag ctc ttc gtc gtt gcc ccc gtg cgc gtc       529
Leu Gln Pro Phe Thr Tyr Glu Leu Phe Val Val Ala Pro Val Arg Val
                165                 170                 175 atc tcg cat gag cgg gcc atc aag ttc gcg ccc atc gga ctc gcc aac       577
Ile Ser His Glu Arg Ala Ile Lys Phe Ala Pro Ile Gly Leu Ala Asn
            180                 185                 190
```

```
atg ctc aac acc gcc ggc gcc gtg cag gcg ttc gag gcc aag aaa gat     625
Met Leu Asn Thr Ala Gly Ala Val Gln Ala Phe Glu Ala Lys Lys Asp
        195                 200                 205 gct agc ggc gtc acg gca gag gtg ttc gtg aag ggc gca ggg gag ctg     673
Ala Ser Gly Val Thr Ala Glu Val Phe Val Lys Gly Ala Gly Glu Leu
    210                 215                 220 gtg gcg tac tcg tcg gcg acg ccc agg ctc tgc aag gtg aac ggc gac     721
Val Ala Tyr Ser Ser Ala Thr Pro Arg Leu Cys Lys Val Asn Gly Asp
225                 230                 235                 240 gag gcc gag ttc acg tac aag gac ggc gtg gtc acc gtc gac gtg ccg     769
Glu Ala Glu Phe Thr Tyr Lys Asp Gly Val Val Thr Val Asp Val Pro
                245                 250                 255 tgg tcg ggg tcg tcg tcg aag ctg tgt tgc gtc cag tac gtc tac         814
Trp Ser Gly Ser Ser Ser Lys Leu Cys Cys Val Gln Tyr Val Tyr
            260                 265                 270 tgagccggac gggccgatga ctctgcgtct ctgctccctg ctggcctgct caggacataa   874
tctaatgttt agagcttacc aggttttaca gctctatcag tttactttttg tttttctgct  934 cttcgttttt taagaattat ttctattgtg tgaattaatg agtgctttcc ttctaaaaa   993

<210> SEQ ID NO 8
<211> LENGTH: 271
<212> TYPE: PRT
<213> ORGANISM: Zea mays

<400> SEQUENCE: 8

Gln Ser Thr His Pro Cys Ala Ala Phe His Ala Ser Arg Ala Ile
1               5                   10                  15

Ser Gly Gly Pro Ile Tyr Val Ser Asp Ser Val Gly Gln His Asp Phe
            20                  25                  30

Ala Leu Leu Arg Arg Leu Ala Leu Pro Asp Gly Thr Val Leu Arg Cys
        35                  40                  45

Glu Gly His Ala Leu Pro Thr Arg Asp Cys Leu Phe Ala Asp Pro Leu
    50                  55                  60

His Asp Gly Arg Thr Val Leu Lys Ile Trp Asn Val Asn Arg Phe Ala
65                  70                  75                  80

Gly Val Val Gly Ala Phe Asn Cys Gln Gly Gly Gly Trp Ser Pro Glu
                85                  90                  95

Ala Arg Arg Asn Lys Cys Phe Ser Glu Phe Ser Val Pro Leu Ala Ala
            100                 105                 110

Arg Ala Ser Pro Ser Asp Val Glu Trp Lys Ser Gly Lys Ala Gly Pro
        115                 120                 125

Gly Val Ser Val Lys Asp Val Ser Gln Phe Ala Val Tyr Ala Val Glu
    130                 135                 140

Ala Arg Thr Leu Gln Leu Leu Arg Pro Asp Glu Gly Val Asp Leu Thr
145                 150                 155                 160

Leu Gln Pro Phe Thr Tyr Glu Leu Phe Val Val Ala Pro Val Arg Val
                165                 170                 175

Ile Ser His Glu Arg Ala Ile Lys Phe Ala Pro Ile Gly Leu Ala Asn
            180                 185                 190

Met Leu Asn Thr Ala Gly Ala Val Gln Ala Phe Glu Ala Lys Lys Asp
        195                 200                 205

Ala Ser Gly Val Thr Ala Glu Val Phe Val Lys Gly Ala Gly Glu Leu
    210                 215                 220

Val Ala Tyr Ser Ser Ala Thr Pro Arg Leu Cys Lys Val Asn Gly Asp
225                 230                 235                 240
```

Glu Ala Glu Phe Thr Tyr Lys Asp Gly Val Val Thr Val Asp Val Pro
                245                 250                 255

Trp Ser Gly Ser Ser Ser Lys Leu Cys Cys Val Gln Tyr Val Tyr
            260                 265                 270

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:synthetic
      primer 1 (from list 1)

<400> SEQUENCE: 9
aattttcaag catagccaag ttaaccacct                                    30

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:synthetic
      primer 2 (from list 1)

<400> SEQUENCE: 10
gctcacaaga taatgatgtt agtc                                          24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:synthetic
      primer 3 (from list 1)

<400> SEQUENCE: 11
atacaagtga ggaacttgac ca                                            22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:synthetic
      primer 4 (from list 1)

<400> SEQUENCE: 12
ccaaaccata gcaaacctaa gcac                                          24

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:synthetic
      primer 5 (from list 1)

<400> SEQUENCE: 13
acaacagaaa aatatgactc ttattact                                      28

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:synthetic primer 6 (from list 1)

<400> SEQUENCE: 14
aaaagagagt caaacatcat agtatc                                          26

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:synthetic
      primer 1 (from list 2)

<400> SEQUENCE: 15
atggcaccac caagcataac caaaactgc                                       29

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence:synthetic
      primer 2 (from list 2)

<400> SEQUENCE: 16
atggcaccac caagcataac caaaactgca accctccaag acg                       43

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:synthetic
      primer 3 (from list 2)

<400> SEQUENCE: 17
tcaaaataaa aactggacca aagac                                           25

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:synthetic
      primer 4 (from list 2)

<400> SEQUENCE: 18
tcaaaataaa aactggacca aagacaatgt                                      30

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:synthetic
      primer 5 (from list 2)

<400> SEQUENCE: 19
atggctccaa gcataagcaa aactg                                           25

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:synthetic
      primer 6 (from list 2)

```
<400> SEQUENCE: 20
atggctccaa gcataagcaa aactgtggaa ct                                32

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:synthetic
      primer 7 (from list 2)

<400> SEQUENCE: 21
tcaaaataaa aactcaacca ttgac                                        25

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence:synthetic
      primer 8 (from list 2)

<400> SEQUENCE: 22
tcaaaataaa aactcaacca ttgacaattt tgaagcact                         39

<210> SEQ ID NO 23
<211> LENGTH: 20
<212> TYPE: PRT
<213> ORGANISM: Vicia faba

<400> SEQUENCE: 23

Gly Ile Lys Phe Met Ser Ile Phe Arg Phe Lys Val Trp Trp Thr Thr
 1               5                  10                  15

His Trp Val Gly
            20

<210> SEQ ID NO 24
<211> LENGTH: 14
<212> TYPE: PRT
<213> ORGANISM: Vicia faba

<400> SEQUENCE: 24

Ile Ile Asp Lys Phe Gly Trp Cys Thr Trp Asp Ala Phe Tyr
 1               5                  10

<210> SEQ ID NO 25
<211> LENGTH: 15
<212> TYPE: PRT
<213> ORGANISM: Vicia faba

<400> SEQUENCE: 25

Gly Gly Cys Pro Pro Gly Phe Val Ile Ile Asp Asp Gly Trp Gln
 1               5                  10                  15

<210> SEQ ID NO 26
<211> LENGTH: 17
<212> TYPE: PRT
<213> ORGANISM: Vicia faba

<400> SEQUENCE: 26

Thr Ser Ala Gly Glu Gln Met Pro Cys Arg Leu Val Lys Tyr Glu Glu
 1               5                  10                  15

Asn
```

```
<210> SEQ ID NO 27
<211> LENGTH: 16
<212> TYPE: PRT
<213> ORGANISM: Vicia faba

<400> SEQUENCE: 27

Val Tyr Val Trp His Ala Leu Cys Gly Tyr Trp Gly Val Arg Pro
  1               5                  10                  15

<210> SEQ ID NO 28
<211> LENGTH: 20
<212> TYPE: PRT
<213> ORGANISM: Vicia faba

<400> SEQUENCE: 28

Thr Met Glu Asp Leu Ala Val Asp Lys Ile Val Glu Asn Gly Val Gly
  1               5                  10                  15

Leu Val Pro Pro
            20

<210> SEQ ID NO 29
<211> LENGTH: 23
<212> TYPE: PRT
<213> ORGANISM: Vicia faba

<400> SEQUENCE: 29

Gly Leu His Ser His Leu Glu Ser Ala Gly Ile Asp Gly Val Lys Val
  1               5                  10                  15

Asp Val Ile His Leu Leu Glu
            20

<210> SEQ ID NO 30
<211> LENGTH: 14
<212> TYPE: PRT
<213> ORGANISM: Vicia faba

<400> SEQUENCE: 30

Gly Gly Arg Val Glu Leu Ala Arg Ala Tyr Tyr Lys Ala Leu
  1               5                  10

<210> SEQ ID NO 31
<211> LENGTH: 12
<212> TYPE: PRT
<213> ORGANISM: Vicia faba

<400> SEQUENCE: 31

Val Lys Lys His Phe Lys Gly Asn Gly Val Ile Ala
  1               5                  10

<210> SEQ ID NO 32
<211> LENGTH: 46
<212> TYPE: PRT
<213> ORGANISM: Vicia faba

<400> SEQUENCE: 32

Glu His Cys Asn Asp Phe Phe Leu Leu Gly Thr Glu Ala Ile Ser Leu
  1               5                  10                  15

Gly Arg Val Gly Asp Asp Phe Trp Cys Ser Asp Pro Ser Gly Asp Pro
                20                  25                  30

Asn Gly Thr Tyr Trp Leu Gln Gly Cys His Met Val His Cys
                35                  40                  45
```

```
<210> SEQ ID NO 33
<211> LENGTH: 43
<212> TYPE: PRT
<213> ORGANISM: Vicia faba

<400> SEQUENCE: 33

Ala Tyr Asn Ser Leu Trp Met Gly Asn Phe Ile Gln Pro Asp Trp Asp
 1               5                  10                  15

Met Phe Gln Ser Thr His Pro Cys Ala Glu Phe His Ala Ala Ser Arg
                20                  25                  30

Ala Ile Ser Gly Gly Pro Ile Tyr Val Ser Asp
         35                  40

<210> SEQ ID NO 34
<211> LENGTH: 9
<212> TYPE: PRT
<213> ORGANISM: Vicia faba

<400> SEQUENCE: 34

Leu Pro Asp Gly Ser Ile Leu Arg Cys
 1               5

<210> SEQ ID NO 35
<211> LENGTH: 24
<212> TYPE: PRT
<213> ORGANISM: Vicia faba

<400> SEQUENCE: 35

Ala Leu Pro Thr Arg Asp Cys Leu Phe Glu Asp Pro Leu His Asn Gly
 1               5                  10                  15

Lys Thr Met Leu Lys Ile Trp Asn
                20

<210> SEQ ID NO 36
<211> LENGTH: 13
<212> TYPE: PRT
<213> ORGANISM: Vicia faba

<400> SEQUENCE: 36

Gly Val Leu Gly Leu Phe Asn Cys Gln Gly Gly Gly Trp
 1               5                  10

<210> SEQ ID NO 37
<211> LENGTH: 9
<212> TYPE: PRT
<213> ORGANISM: Vicia faba

<400> SEQUENCE: 37

Phe Ala Pro Ile Gly Leu Val Asn Met
 1               5

<210> SEQ ID NO 38
<211> LENGTH: 32
<212> TYPE: DNA
<213> ORGANISM: Artificial Sequence
<220> FEATURE:
<221> NAME/KEY: modified_base
<222> LOCATION: (1)..(32)
<223> OTHER INFORMATION: n = inosine
<223> OTHER INFORMATION: Description of Artificial Sequence:synthetic
      primer 1-F (from list 4)

<400> SEQUENCE: 38
ttnaangtnt ggtggacnac ncantgggtn gg                                32
```

<210> SEQ ID NO 39
<211> LENGTH: 41
<212> TYPE: DNA
<213> ORGANISM: Artificial Sequence
<220> FEATURE:
<221> NAME/KEY: modified_base
<222> LOCATION: (1)..(41)
<223> OTHER INFORMATION: n = inosine
<223> OTHER INFORMATION: Description of Artificial Sequence:synthetic
      primer 2-F (from list 4)

<400> SEQUENCE: 39
atnatngana anttnggntg gtgnacntgg gangcnttnt a                     41

<210> SEQ ID NO 40
<211> LENGTH: 41
<212> TYPE: DNA
<213> ORGANISM: Artificial Sequence
<220> FEATURE:
<221> NAME/KEY: modified_base
<222> LOCATION: (1)..(41)
<223> OTHER INFORMATION: n = inosine
<223> OTHER INFORMATION: Description of Artificial Sequence:synthetic
      primer 2-RV (from list 4)

<400> SEQUENCE: 40
tanaangcnt cccangtnca ccanccnaan ttntcnatna t                     41

<210> SEQ ID NO 41
<211> LENGTH: 44
<212> TYPE: DNA
<213> ORGANISM: Artificial Sequence
<220> FEATURE:
<221> NAME/KEY: modified_base
<222> LOCATION: (1)..(44)
<223> OTHER INFORMATION: n = inosine
<223> OTHER INFORMATION: Description of Artificial Sequence:synthetic
      primer 3-F (from list 4)

<400> SEQUENCE: 41
ggnggntgnc cnccnggntt ngtnatnatn ganganggnt ggca                  44

<210> SEQ ID NO 42
<211> LENGTH: 44
<212> TYPE: DNA
<213> ORGANISM: Artificial Sequence
<220> FEATURE:
<221> NAME/KEY: modified_base
<222> LOCATION: (1)..(44)
<223> OTHER INFORMATION: n = inosine
<223> OTHER INFORMATION: Description of Artificial Sequence:synthetic
      primer 3-RV (from list 4)

<400> SEQUENCE: 42
tgccanccnt cntcnatnat nacnaanccn ggnggncanc cncc                  44

<210> SEQ ID NO 43
<211> LENGTH: 32
<212> TYPE: DNA
<213> ORGANISM: Artificial Sequence
<220> FEATURE:
<221> NAME/KEY: modified_base
<222> LOCATION: (1)..(32)
<223> OTHER INFORMATION: n = inosine
<223> OTHER INFORMATION: Description of Artificial Sequence:synthetic
      primer 4-F (from list 4)

<400> SEQUENCE: 43
aanaancant tnaanggnaa nggngtnatn gc                          32

<210> SEQ ID NO 44
<211> LENGTH: 32
<212> TYPE: DNA
<213> ORGANISM: Artificial Sequence
<220> FEATURE:
<221> NAME/KEY: modified_base
<222> LOCATION: (1)..(32)
<223> OTHER INFORMATION: n = inosine
<223> OTHER INFORMATION: Description of Artificial Sequence:synthetic
      primer 4-RV (from list 4)

<400> SEQUENCE: 44
gcnatnacnc cnttnccntt naantgnttn tt                          32

<210> SEQ ID NO 45
<211> LENGTH: 38
<212> TYPE: DNA
<213> ORGANISM: Artificial Sequence
<220> FEATURE:
<221> NAME/KEY: modified_base
<222> LOCATION: (1)..(38)
<223> OTHER INFORMATION: n = inosine
<223> OTHER INFORMATION: Description of Artificial Sequence:synthetic
      primer 5-F (from list 4)

<400> SEQUENCE: 45
tggatgggna anttnatnca nccngantgg ganatgtt                    38

<210> SEQ ID NO 46
<211> LENGTH: 38
<212> TYPE: DNA
<213> ORGANISM: Artificial Sequence
<220> FEATURE:
<221> NAME/KEY: modified_base
<222> LOCATION: (1)..(38)
<223> OTHER INFORMATION: n = inosine
<223> OTHER INFORMATION: Description of Artificial Sequence:synthetic
      primer 5-RV (from list 4)

<400> SEQUENCE: 46
aacatntccc antcnggntg natnaanttn cccatcca                    38

<210> SEQ ID NO 47
<211> LENGTH: 27
<212> TYPE: DNA
<213> ORGANISM: Artificial Sequence
<220> FEATURE:
<221> NAME/KEY: modified_base
<222> LOCATION: (1)..(27)
<223> OTHER INFORMATION: n = inosine
<223> OTHER INFORMATION: Description of Artificial Sequence:synthetic
      primer 6-RV (from list 4)

<400> SEQUENCE: 47
catnttnacn arnccnatng gngcnaa                                27

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence:synthetic
      primer 8.2 (from list 5)

<400> SEQUENCE: 48
aaracngcnc cnagyathat hgacaa                                 26

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:synthetic primer 13.4 (from list 5)

<400> SEQUENCE: 49
aarathtgga ayctnaacaa                                              20

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:synthetic primer 7.4 (from list 5)

<400> SEQUENCE: 50
aargcnagrg tngtngtncc naag                                         24

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence:synthetic primer 13.3RV (from list 5)

<400> SEQUENCE: 51
yttrttnagr ttccadattt t                                            21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence:synthetic primer 10.3RV (from list 5)

<400> SEQUENCE: 52
yttrtcytcr tanagraatt t                                            21

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence:synthetic primer RES-2RV (from list 6)

<400> SEQUENCE: 53
ggctgaggtt cggttcattc ctgaatcatc                                   30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence:synthetic primer RS-7 (from list 6)

<400> SEQUENCE: 54
ccaaatggta catattggct ccaaggttgt                                   30

```
<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence:synthetic
      primer RS-8 (from list 6)

<400> SEQUENCE: 55
aagagtgtat ctgaattttc acgcgcggtg                                    30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence:synthetic
      primer RS-9 (from list 6)

<400> SEQUENCE: 56
tggtgcaatg ggaaaactcc aatgagcacc                                    30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence:synthetic
      primer RS-10 (from list 6)

<400> SEQUENCE: 57
atgaagtgtt ctgatagatt gaaagtttcg                                    30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence:synthetic
      primer RS-11 (from list 6)

<400> SEQUENCE: 58
cagtctctgg agtttgatga taatgcaagt                                    30

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence:synthetic
      primer RS-N (from list 7)

<400> SEQUENCE: 59
cgcggatcca ccatggcacc accaagcata accaaaactg c                       41

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence:synthetic
      primer RS-C (from list 7)
<221> NAME/KEY: modified_base
<222> LOCATION: (1)..(37)
<223> OTHER INFORMATION: n = inosine

<400> SEQUENCE: 60
tgctctagat tatcaaaata aaaactggac caaagac                            37
```

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence:synthetic
    primer 1-F (from list 8)
<221> NAME/KEY: modified_base
<222> LOCATION: (1)..(35)
<223> OTHER INFORMATION: n= inosine

<400> SEQUENCE: 61
cgattnaang tntggtggac nacncantgg gtngg                          35

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence:synthetic
    primer 2-RV (from list 8)
<221> NAME/KEY: modified_base
<222> LOCATION: (1)..(45)
<223> OTHER INFORMATION: n = inosine

<400> SEQUENCE: 62
ggcctanaan gcntcccang tncaccancc naanttntcn atnat               45

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence:synthetic
    primer 5-F (from list 8)
<221> NAME/KEY: modified_base
<222> LOCATION: (1)..(41)
<223> OTHER INFORMATION: n = inosine

<400> SEQUENCE: 63
cgatggatgg gnaanttnat ncanccngan tggganatgt t                   41

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence:synthetic
    primer 6-RV (from list 8)
<221> NAME/KEY: modified_base
<222> LOCATION: (1)..(32)
<223> OTHER INFORMATION: n = inosine

<400> SEQUENCE: 64
ggccacatnt tnacnarncc natnggngcn aa                             32

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence:synthetic
    primer SN-1 (from list 9)

<400> SEQUENCE: 65
cacgaactgg ggcacgagac acagatgatg                                30

```
<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence:synthetic
      primer SC-3RV (from list 9)

<400> SEQUENCE: 66
aagcaagtca cggagtgtga atagtcagag                                      30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence:synthetic
      primer SC-5 (from list 9)

<400> SEQUENCE: 67
acacgagact gtttgtttga agaccccttg                                      30

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence:synthetic
      primer SC-6 (from list 9)

<400> SEQUENCE: 68
tggaatctca acaaatatac aggtg                                           25

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:synthetic
      primer SN-3RV (from list 9)

<400> SEQUENCE: 69
gggtcatggc caacgtggac gtataagcac                                      30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence:synthetic
      primer SN-4RV (from list 9)

<400> SEQUENCE: 70
gatgatcact ggcgcggttt tctcctcgag                                      30

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence:synthetic
      primer 1-F (from list 10)
<221> NAME/KEY: modified_base
<222> LOCATION: (1)..(35)
<223> OTHER INFORMATION: n = inosine

<400> SEQUENCE: 71
cgattnaang tntggtggac nacncantgg gtngg                                35
```

<210> SEQ ID NO 72
<211> LENGTH: 37
<212> TYPE: DNA
<213> ORGANISM: Artificial Sequence
<220> FEATURE:
<223> OTHER INFORMATION: Description of Artificial Sequence:synthetic primer 4-RV (from list 10)
<221> NAME/KEY: modified_base
<222> LOCATION: (1)..(37)
<223> OTHER INFORMATION: n = inosine

<400> SEQUENCE: 72
ggccagcnat nacnccnttn ccnttnaant gnttntt                                37

<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence:synthetic primer 2-F (from list 10)
<221> NAME/KEY: modified_base
<222> LOCATION: (1)..(44)
<223> OTHER INFORMATION: n = inosine

<400> SEQUENCE: 73
cgaatnatng anaanttngg ntggtgnacn tgggangcnt tnta                        44

<210> SEQ ID NO 74
<211> LENGTH: 32
<212> TYPE: DNA
<213> ORGANISM: Artificial Sequence
<220> FEATURE:
<223> OTHER INFORMATION: Description of Artificial Sequence:synthetic primer 6-RV (from list 10)
<221> NAME/KEY: modified_base
<222> LOCATION: (1)..(32)
<223> OTHER INFORMATION: n = inosine

<400> SEQUENCE: 74
ggccacatnt tnacnarncc natnggngcn aa                                     32

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence:synthetic primer 5-F (from list 11)
<221> NAME/KEY: modified_base
<222> LOCATION: (1)..(41)
<223> OTHER INFORMATION: n= inosine

<400> SEQUENCE: 75
cgatggatgg gnaanttnat ncanccngan tggganatgt t                           41

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence:synthetic primer 6-RV (from list 11)
<221> NAME/KEY: modified_base
<222> LOCATION: (1)..(32)
<223> OTHER INFORMATION: n = inosine

<400> SEQUENCE: 76

```
ggccacatnt tnacnarncc natnggngcn aa                                     32
```

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence:synthetic
      primer M10 (from list 12)

<400> SEQUENCE: 77

```
gacgtcgagt ggaagagcgg caagg                                             25
```

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence:synthetic
      primer M-11 (from list 12)

<400> SEQUENCE: 78

```
cacctacgag ctcttcgtcg ttgcc                                             25
```

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence:synthetic
      primer BamSac-(+) (from list 13)

<400> SEQUENCE: 79

```
gatcgagctc gtgtcggatc cagct                                             25
```

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence:synthetic
      primer BamSac-(-) (from list 13)

<400> SEQUENCE: 80

```
ggatccgaca cgagctc                                                      17
```

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence:synthetic
      primer 35S (from list 14)

<400> SEQUENCE: 81

```
ttccagtatg gacgattcaa ggcttgcttc                                        30
```

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence:synthetic
      primer NOS (from list 14)

<400> SEQUENCE: 82

```
atgtataatt gcgggactct aatca                                             25
```

```
<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence:synthetic
      primer RS-F (from list 14)

<400> SEQUENCE: 83
aagagtgtat ctgaattttc acgcgcggtg                                       30

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence:synthetic
      primer RS-RV (from list 14)

<400> SEQUENCE: 84
accttcccat acacctttg gatgaacctt caa                                    33

<210> SEQ ID NO 85
<211> LENGTH: 38
<212> TYPE: DNA
<213> ORGANISM: Artificial Sequence
<220> FEATURE:
<223> OTHER INFORMATION: Description of Artificial Sequence:BamHI-NcoI
      linker (from Fig. 1)

<400> SEQUENCE: 85
ggatccacca tggcaccacc aagcataacc aaaactgc                              38

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence:
      XbaI-NotI-SacI linker (from Fig. 1)

<400> SEQUENCE: 86
tgataatcta gagcggccgc caccgcggtg gagctc                                36

<210> SEQ ID NO 87
<211> LENGTH: 34
<212> TYPE: DNA
<213> ORGANISM: Artificial Sequence
<220> FEATURE:
<223> OTHER INFORMATION: Description of Artificial Sequence:
      XbaI-NotI-SacI linker (from Fig. 1)

<400> SEQUENCE: 87
tctagattat caaaataaaa actggaccaa agac                                  34
```